US009125756B2

(12) United States Patent
Ullrich, Jr. et al.

(10) Patent No.: US 9,125,756 B2
(45) Date of Patent: Sep. 8, 2015

(54) PROCESSES FOR PRODUCING REGULAR REPEATING PATTERNS ON SURFACES OF INTERBODY DEVICES

(75) Inventors: Peter F. Ullrich, Jr., Neenah, WI (US); Chad J. Patterson, Port Washington, WI (US)

(73) Assignee: Titan Spine, LLC, Mequon, WI (US)

( * ) Notice: Subject to any disclaimer, the term of this patent is extended or adjusted under 35 U.S.C. 154(b) by 264 days.

(21) Appl. No.: 13/566,357

(22) Filed: Aug. 3, 2012

(65) Prior Publication Data
US 2012/0312778 A1    Dec. 13, 2012

Related U.S. Application Data

(63) Continuation-in-part of application No. 12/151,198, filed on May 5, 2008, now Pat. No. 8,262,737, which is a continuation-in-part of application No. 11/123,359, filed on May 6, 2005, now Pat. No. 7,662,186.

(51) Int. Cl.
*A61F 2/44* (2006.01)
*A61F 2/30* (2006.01)
(Continued)

(52) U.S. Cl.
CPC .......... *A61F 2/4455* (2013.01); *A61F 2/30965* (2013.01); *A61F 2/4465* (2013.01);
(Continued)

(58) Field of Classification Search
CPC ....... A61F 2/44; A61F 2/4455; A61F 2/4465; A61F 2002/4475; A61F 2002/30838; A61F 2002/3084; A61F 2002/30892; A61F 2002/30906; A61F 2002/3025; Y10T 29/49888; Y10T 29/49995; Y10T 29/49996

USPC .......................................... 623/17.11–17.16
See application file for complete search history.

(56) References Cited

U.S. PATENT DOCUMENTS 4,314,876 A    2/1982   Kremer et al.
4,834,757 A    5/1989   Brantigan
(Continued)

FOREIGN PATENT DOCUMENTS

EP    0599419    6/1994
EP    0916323    5/1999
(Continued)

OTHER PUBLICATIONS

Astra Tech Dental, "Nanolevel topographic modifications on the OsseoSpeed surface", http://shop.dentsplyimplants.us, Mar. 8, 2001.
(Continued)

*Primary Examiner* — Eduardo C. Robert
*Assistant Examiner* — Julianna N Harvey
(74) *Attorney, Agent, or Firm* — Stradley Ronon Stevens & Young, LLP

(57) ABSTRACT

Processes for producing interbody spinal implants having a body with a top surface, a bottom surface, opposing lateral sides, opposing anterior and posterior portions, a substantially hollow center, and a single vertical aperture; and optionally, one or two integration plates affixed to the body. The processes include applying an additive process, a subtractive process, or both processes to at least one surface of the interbody spinal implant to form a roughened surface topography having a regular repeating pattern. The roughened surface topography is specifically designed to provide certain frictional characteristics, load dispersion, and to influence the biological responses that occur during bone healing and fusion.

20 Claims, 21 Drawing Sheets

(51) Int. Cl.
*A61F 2/28* (2006.01)
*A61F 2/46* (2006.01)

(52) U.S. Cl.
CPC ...... *A61F 2/4611* (2013.01); *A61F 2002/2817* (2013.01); *A61F 2002/2835* (2013.01); *A61F 2002/305* (2013.01); *A61F 2002/30013* (2013.01); *A61F 2002/30014* (2013.01); *A61F 2002/3084* (2013.01); *A61F 2002/3093* (2013.01); *A61F 2002/3097* (2013.01); *A61F 2002/30133* (2013.01); *A61F 2002/30273* (2013.01); *A61F 2002/30321* (2013.01); *A61F 2002/30405* (2013.01); *A61F 2002/30441* (2013.01); *A61F 2002/30454* (2013.01); *A61F 2002/30469* (2013.01); *A61F 2002/30472* (2013.01); *A61F 2002/30481* (2013.01); *A61F 2002/30507* (2013.01); *A61F 2002/30604* (2013.01); *A61F 2002/30769* (2013.01); *A61F 2002/30772* (2013.01); *A61F 2002/30774* (2013.01); *A61F 2002/30779* (2013.01); *A61F 2002/30785* (2013.01); *A61F 2002/30787* (2013.01); *A61F 2002/30789* (2013.01); *A61F 2002/30836* (2013.01); *A61F 2002/30838* (2013.01); *A61F 2002/30892* (2013.01); *A61F 2002/30906* (2013.01); *A61F 2002/30925* (2013.01); *A61F 2002/30927* (2013.01); *A61F 2002/30973* (2013.01); *A61F 2002/30985* (2013.01); *A61F 2002/448* (2013.01); *A61F 2002/4475* (2013.01); *A61F 2002/4629* (2013.01); *A61F 2310/00017* (2013.01); *A61F 2310/00023* (2013.01); *A61F 2310/00047* (2013.01); *A61F 2310/00053* (2013.01); *A61F 2310/00131* (2013.01); *A61F 2310/00407* (2013.01); *Y10T 29/49888* (2015.01); *Y10T 29/49995* (2015.01)

(56) References Cited

U.S. PATENT DOCUMENTS

| | | | |
|---|---|---|---|
| 4,904,261 A | 2/1990 | Dove et al. | |
| 5,015,247 A | 5/1991 | Michelson | |
| 5,071,437 A | 12/1991 | Steffee | |
| 5,258,098 A * | 11/1993 | Wagner et al. | 216/52 |
| 5,306,308 A | 4/1994 | Gross et al. | |
| 5,306,309 A | 4/1994 | Wagner et al. | |
| 5,425,772 A | 6/1995 | Brantigan | |
| 5,443,514 A | 8/1995 | Steffee | |
| 5,456,723 A | 10/1995 | Steinemann et al. | |
| 5,507,815 A | 4/1996 | Wagner et al. | |
| 5,571,188 A | 11/1996 | Ellingsen et al. | |
| 5,603,338 A | 2/1997 | Beaty | |
| 5,609,635 A | 3/1997 | Michelson | |
| 5,702,449 A | 12/1997 | McKay | |
| 5,755,798 A | 5/1998 | Papavero et al. | |
| 5,766,252 A | 6/1998 | Henry et al. | |
| 5,776,199 A | 7/1998 | Michelson | |
| 5,860,973 A | 1/1999 | Michelson | |
| 5,863,201 A | 1/1999 | Lazzara et al. | |
| 5,865,845 A | 2/1999 | Thalgott | |
| 5,876,453 A | 3/1999 | Beaty | |
| 5,885,079 A | 3/1999 | Niznick | |
| 5,888,224 A | 3/1999 | Beckers et al. | |
| 5,922,029 A | 7/1999 | Wagner et al. | |
| 5,968,098 A | 10/1999 | Winslow | |
| 5,984,922 A | 11/1999 | McKay | |
| 6,033,582 A | 3/2000 | Lee et al. | |
| 6,039,762 A | 3/2000 | McKay | |
| 6,059,829 A | 5/2000 | Schlaepfer et al. | |
| 6,080,158 A | 6/2000 | Lin | |
| 6,086,613 A | 7/2000 | Camino et al. | |
| 6,096,107 A | 8/2000 | Caracostas et al. | |
| 6,123,705 A | 9/2000 | Michelson | |
| 6,143,032 A | 11/2000 | Schafer et al. | |
| 6,176,882 B1 | 1/2001 | Biedermann et al. | |
| 6,183,255 B1 | 2/2001 | Oshida | |
| 6,193,757 B1 | 2/2001 | Foley et al. | |
| 6,193,762 B1 | 2/2001 | Wagner et al. | |
| 6,241,770 B1 | 6/2001 | Michelson | |
| 6,241,771 B1 | 6/2001 | Gresser et al. | |
| 6,245,108 B1 | 6/2001 | Biscup | |
| 6,296,664 B1 | 10/2001 | Middleton | |
| 6,302,914 B1 | 10/2001 | Michelson | |
| 6,342,074 B1 | 1/2002 | Simpson | |
| 6,344,057 B1 | 2/2002 | Rabbe et al. | |
| 6,350,283 B1 | 2/2002 | Michelson | |
| 6,375,681 B1 | 4/2002 | Truscott | |
| 6,387,130 B1 | 5/2002 | Stone et al. | |
| 6,395,031 B1 | 5/2002 | Foley et al. | |
| 6,423,095 B1 | 7/2002 | Van Hoeck et al. | |
| 6,425,920 B1 | 7/2002 | Hamada | |
| 6,432,140 B1 | 8/2002 | Lin | |
| 6,436,102 B1 | 8/2002 | Ralph et al. | |
| 6,447,544 B1 | 9/2002 | Michelson | |
| 6,458,159 B1 | 10/2002 | Thalgott | |
| 6,478,823 B1 | 11/2002 | Michelson | |
| 6,482,233 B1 | 11/2002 | Aebi et al. | |
| 6,485,517 B1 | 11/2002 | Michelson | |
| 6,491,723 B1 | 12/2002 | Beaty | |
| 6,520,993 B2 | 2/2003 | James et al. | |
| 6,558,424 B2 | 5/2003 | Thalgott | |
| 6,569,201 B2 | 5/2003 | Moumene et al. | |
| 6,579,318 B2 | 6/2003 | Varga et al. | |
| 6,592,624 B1 | 7/2003 | Fraser et al. | |
| 6,599,322 B1 | 7/2003 | Amrich et al. | |
| 6,610,089 B1 | 8/2003 | Liu et al. | |
| 6,620,332 B2 | 9/2003 | Amrich | |
| 6,635,086 B2 | 10/2003 | Lin | |
| 6,652,765 B1 | 11/2003 | Beaty | |
| 6,676,703 B2 | 1/2004 | Biscup | |
| 6,702,855 B1 | 3/2004 | Steinemann et al. | |
| 6,719,794 B2 | 4/2004 | Gerber et al. | |
| 6,726,720 B2 | 4/2004 | Ross et al. | |
| 6,730,127 B2 | 5/2004 | Michelson | |
| 6,740,118 B2 | 5/2004 | Eisermann et al. | |
| 6,743,231 B1 | 6/2004 | Gray et al. | |
| 6,758,849 B1 | 7/2004 | Michelson | |
| 6,833,006 B2 | 12/2004 | Foley et al. | |
| 6,890,355 B2 | 5/2005 | Michelson | |
| 6,902,581 B2 | 6/2005 | Walkenhorst et al. | |
| 6,911,249 B2 | 6/2005 | Wagner et al. | |
| 6,923,810 B1 | 8/2005 | Michelson | |
| 6,964,687 B1 | 11/2005 | Bernard et al. | |
| 6,974,480 B2 | 12/2005 | Messerli et al. | |
| 6,981,975 B2 | 1/2006 | Michelson | |
| 7,018,412 B2 | 3/2006 | Ferreira et al. | |
| 7,018,418 B2 | 3/2006 | Amrich et al. | |
| 7,041,137 B2 | 5/2006 | Fulton et al. | |
| 7,044,972 B2 | 5/2006 | Mathys, Jr. et al. | |
| 7,048,870 B1 | 5/2006 | Ellingsen et al. | |
| 7,060,073 B2 | 6/2006 | Frey et al. | |
| 7,066,961 B2 | 6/2006 | Michelson | |
| 7,077,864 B2 | 7/2006 | Byrd, III et al. | |
| 7,087,085 B2 | 8/2006 | Steinemann et al. | |
| 7,112,224 B2 | 9/2006 | Liu et al. | |
| 7,128,760 B2 | 10/2006 | Michelson | |
| 7,137,997 B2 | 11/2006 | Paul | |
| 7,141,068 B2 | 11/2006 | Ross et al. | |
| 7,144,428 B2 | 12/2006 | Anitua | |
| 7,166,129 B2 | 1/2007 | Michelson | |
| 7,169,183 B2 | 1/2007 | Liu et al. | |
| D539,934 S | 4/2007 | Blain | |
| 7,201,775 B2 | 4/2007 | Gorensek et al. | |
| D541,940 S | 5/2007 | Blain | |
| 7,220,280 B2 | 5/2007 | Kast et al. | |
| 7,223,289 B2 | 5/2007 | Trieu et al. | |
| 7,226,480 B2 | 6/2007 | Thalgott | |
| 7,238,186 B2 | 7/2007 | Zdeblick et al. | |
| 7,244,275 B2 | 7/2007 | Michelson | |
| 7,250,060 B2 | 7/2007 | Trieu | |

(56) References Cited

U.S. PATENT DOCUMENTS

| | | |
|---|---|---|
| 7,255,698 B2 | 8/2007 | Michelson |
| 7,288,093 B2 | 10/2007 | Michelson |
| 7,311,734 B2 | 12/2007 | Van Hoeck et al. |
| D564,095 S | 3/2008 | Blain |
| 7,347,873 B2 | 3/2008 | Paul et al. |
| D566,276 S | 4/2008 | Blain |
| 7,368,065 B2 | 5/2008 | Yang et al. |
| 7,410,501 B2 | 8/2008 | Michelson |
| 7,501,073 B2 | 3/2009 | Wen et al. |
| 7,503,933 B2 | 3/2009 | Michelson |
| 7,517,363 B2 | 4/2009 | Rogers et al. |
| D599,019 S | 8/2009 | Pimenta et al. |
| 7,569,074 B2 | 8/2009 | Eisermann et al. |
| 7,608,107 B2 | 10/2009 | Michelson |
| 7,615,078 B2 | 11/2009 | White et al. |
| 7,655,042 B2 | 2/2010 | Foley et al. |
| 7,662,186 B2 | 2/2010 | Bagga et al. |
| 7,662,190 B2 | 2/2010 | Steinemann et al. |
| 7,744,612 B2 | 6/2010 | Blain |
| 7,846,183 B2 | 12/2010 | Blain |
| 7,901,462 B2 | 3/2011 | Yang et al. |
| 7,998,172 B2 | 8/2011 | Blain |
| 8,062,304 B2 | 11/2011 | Blain et al. |
| 8,100,955 B2 | 1/2012 | Blain et al. |
| 8,142,355 B2 | 3/2012 | Blain et al. |
| 8,172,854 B2 | 5/2012 | Blain et al. |
| 8,262,737 B2 | 9/2012 | Bagga et al. |
| 2001/0014826 A1 | 8/2001 | Biedermann et al. |
| 2001/0016777 A1 | 8/2001 | Biscup |
| 2001/0039454 A1 | 11/2001 | Ricci et al. |
| 2001/0047208 A1 | 11/2001 | Michelson |
| 2002/0049497 A1 | 4/2002 | Mason |
| 2002/0087212 A1 | 7/2002 | James et al. |
| 2002/0099443 A1 | 7/2002 | Messerli et al. |
| 2002/0128716 A1 | 9/2002 | Cohen et al. |
| 2002/0138142 A1 | 9/2002 | Castro et al. |
| 2002/0156529 A1 | 10/2002 | Li et al. |
| 2002/0161443 A1 | 10/2002 | Michelson |
| 2002/0173854 A1 | 11/2002 | Amrich |
| 2002/0188294 A1 | 12/2002 | Couture et al. |
| 2003/0014116 A1 | 1/2003 | Ralph et al. |
| 2003/0065401 A1* | 4/2003 | Amrich et al. ............ 623/23.55 |
| 2003/0083668 A1 | 5/2003 | Rogers et al. |
| 2003/0105527 A1 | 6/2003 | Bresina |
| 2003/0109928 A1 | 6/2003 | Pasquet et al. |
| 2003/0118858 A1* | 6/2003 | Kushida et al. ............ 428/627 |
| 2003/0125739 A1 | 7/2003 | Bagga et al. |
| 2003/0153975 A1 | 8/2003 | Byrd, III et al. |
| 2003/0176925 A1 | 9/2003 | Paponneau |
| 2003/0181980 A1 | 9/2003 | Berry et al. |
| 2003/0181981 A1 | 9/2003 | Lemaire |
| 2003/0187506 A1 | 10/2003 | Ross et al. |
| 2003/0191531 A1 | 10/2003 | Berry et al. |
| 2004/0073314 A1 | 4/2004 | White et al. |
| 2004/0117019 A1 | 6/2004 | Trieu et al. |
| 2004/0117020 A1 | 6/2004 | Frey et al. |
| 2004/0122518 A1 | 6/2004 | Rhoda |
| 2004/0127993 A1 | 7/2004 | Kast et al. |
| 2004/0134886 A1 | 7/2004 | Wagner et al. |
| 2004/0153154 A1 | 8/2004 | Dinkelacker |
| 2004/0153160 A1 | 8/2004 | Carrasco |
| 2004/0162616 A1 | 8/2004 | Simonton et al. |
| 2004/0167632 A1 | 8/2004 | Wen et al. |
| 2004/0210309 A1 | 10/2004 | Denzer et al. |
| 2004/0230306 A1 | 11/2004 | Hoeck et al. |
| 2004/0265780 A1 | 12/2004 | Robb et al. |
| 2004/0267367 A1 | 12/2004 | O'Neil |
| 2005/0021150 A1 | 1/2005 | Michelson |
| 2005/0027360 A1* | 2/2005 | Webb et al. ............ 623/17.11 |
| 2005/0038512 A1 | 2/2005 | Michelson |
| 2005/0060034 A1 | 3/2005 | Berry et al. |
| 2005/0075734 A1 | 4/2005 | Fulton et al. |
| 2005/0085913 A1 | 4/2005 | Fraser et al. |
| 2005/0119758 A1 | 6/2005 | Alexander et al. |
| 2005/0131416 A1 | 6/2005 | Jansen et al. |
| 2005/0147942 A1 | 7/2005 | Hall |
| 2005/0159814 A1 | 7/2005 | Karahalios |
| 2005/0161120 A1 | 7/2005 | Inagaki et al. |
| 2005/0165483 A1 | 7/2005 | Ray et al. |
| 2005/0203630 A1 | 9/2005 | Pope et al. |
| 2005/0251257 A1 | 11/2005 | Mitchell et al. |
| 2006/0041313 A1 | 2/2006 | Allard et al. |
| 2006/0093646 A1 | 5/2006 | Cima et al. |
| 2006/0100705 A1 | 5/2006 | Puno et al. |
| 2006/0149372 A1 | 7/2006 | Paxson et al. |
| 2006/0149376 A1 | 7/2006 | Shimp et al. |
| 2006/0167549 A1 | 7/2006 | Mathys, Jr. et al. |
| 2006/0190079 A1 | 8/2006 | Istephanous et al. |
| 2006/0219661 A1 | 10/2006 | Towse et al. |
| 2006/0235534 A1 | 10/2006 | Gertzman et al. |
| 2006/0265065 A1 | 11/2006 | Bagga et al. |
| 2006/0293748 A1 | 12/2006 | Alexander et al. |
| 2007/0010885 A1 | 1/2007 | Liu et al. |
| 2007/0093898 A1 | 4/2007 | Schwab et al. |
| 2007/0118220 A1 | 5/2007 | Liu et al. |
| 2007/0118223 A1 | 5/2007 | Allard et al. |
| 2007/0233247 A1 | 10/2007 | Schwab |
| 2007/0233248 A1 | 10/2007 | Schwab et al. |
| 2007/0260320 A1 | 11/2007 | Peterman et al. |
| 2007/0269475 A1 | 11/2007 | Gil et al. |
| 2007/0270951 A1 | 11/2007 | Davis et al. |
| 2007/0270956 A1 | 11/2007 | Heinz |
| 2007/0282441 A1 | 12/2007 | Stream et al. |
| 2007/0288028 A1 | 12/2007 | Gorensek et al. |
| 2007/0293949 A1 | 12/2007 | Salerni et al. |
| 2008/0014243 A1 | 1/2008 | Ellingsen et al. |
| 2008/0071380 A1 | 3/2008 | Sweeney |
| 2008/0077171 A1 | 3/2008 | Blain et al. |
| 2008/0097610 A1 | 4/2008 | Guyer et al. |
| 2008/0154378 A1 | 6/2008 | Pelo |
| 2008/0195209 A1 | 8/2008 | Garcia et al. |
| 2008/0221689 A1 | 9/2008 | Chaput et al. |
| 2008/0249622 A1 | 10/2008 | Gray |
| 2008/0262623 A1 | 10/2008 | Bagga et al. |
| 2008/0269764 A1 | 10/2008 | Blain et al. |
| 2008/0269806 A1 | 10/2008 | Zhang et al. |
| 2008/0288076 A1 | 11/2008 | Soo et al. |
| 2009/0005784 A1 | 1/2009 | Blain et al. |
| 2009/0005871 A1 | 1/2009 | White et al. |
| 2009/0014243 A1 | 1/2009 | Whigham |
| 2009/0024132 A1 | 1/2009 | Blain et al. |
| 2009/0082819 A1 | 3/2009 | Blain et al. |
| 2009/0088800 A1 | 4/2009 | Blain et al. |
| 2009/0088853 A1 | 4/2009 | Ogilvie et al. |
| 2009/0132048 A1 | 5/2009 | Denzer |
| 2009/0182432 A1 | 7/2009 | Zdeblick et al. |
| 2009/0187247 A1 | 7/2009 | Metcalf, Jr. et al. |
| 2009/0204152 A1 | 8/2009 | Blain |
| 2009/0234362 A1 | 9/2009 | Blain et al. |
| 2009/0264928 A1 | 10/2009 | Blain |
| 2009/0276049 A1 | 11/2009 | Weiland |
| 2009/0312837 A1 | 12/2009 | Eisermann et al. |
| 2010/0076559 A1 | 3/2010 | Bagga et al. |
| 2010/0094426 A1 | 4/2010 | Grohowski, Jr. et al. |
| 2010/0121385 A1 | 5/2010 | Blain et al. |
| 2010/0173264 A1 | 7/2010 | Fredriksson et al. |
| 2010/0204798 A1 | 8/2010 | Gerbec et al. |
| 2010/0218854 A1 | 9/2010 | Garcia Saban et al. |
| 2010/0228288 A1 | 9/2010 | Blain |
| 2010/0249937 A1 | 9/2010 | Blain et al. |
| 2010/0274286 A1 | 10/2010 | Blain et al. |
| 2010/0274358 A1 | 10/2010 | Mueller et al. |
| 2010/0303722 A1 | 12/2010 | Jin et al. |
| 2011/0009965 A1 | 1/2011 | Ankem |
| 2011/0040301 A1 | 2/2011 | Blain et al. |
| 2011/0082503 A1 | 4/2011 | Blain |
| 2011/0190902 A1 | 8/2011 | Tong et al. |
| 2011/0224796 A1 | 9/2011 | Weiland et al. |
| 2011/0230970 A1 | 9/2011 | Lynn et al. |
| 2011/0233169 A1 | 9/2011 | Mayfield et al. |
| 2011/0282454 A1 | 11/2011 | Ullrich, Jr. et al. |
| 2012/0009341 A1 | 1/2012 | Noh et al. |
| 2012/0046695 A9 | 2/2012 | Blain |
| 2012/0123424 A1 | 5/2012 | Blain et al. |

(56) References Cited

U.S. PATENT DOCUMENTS

| | | |
|---|---|---|
| 2012/0123548 A1 | 5/2012 | Lynn et al. |
| 2012/0136443 A1 | 5/2012 | Wentzel |
| 2012/0149991 A1 | 6/2012 | Blain et al. |
| 2012/0158056 A1 | 6/2012 | Blain |
| 2012/0158144 A1 | 6/2012 | Ullrich, Jr. et al. |
| 2012/0172991 A1 | 7/2012 | Bertele et al. |
| 2012/0232664 A1 | 9/2012 | Ulrich, Jr. et al. |
| 2012/0239150 A1 | 9/2012 | Ullrich, Jr. et al. |
| 2012/0239151 A1 | 9/2012 | Ulrich, Jr. et al. |
| 2012/0239152 A1 | 9/2012 | Ullrich, Jr. et al. |
| 2012/0239153 A1 | 9/2012 | Ullrich, Jr. et al. |
| 2012/0239154 A1 | 9/2012 | Ullrich, Jr. et al. |
| 2012/0245694 A1 | 9/2012 | Ullrich, Jr. et al. |
| 2012/0277876 A1 | 11/2012 | Ullrich, Jr. et al. |
| 2012/0303127 A1 | 11/2012 | Ullrich, Jr. et al. |
| 2012/0303128 A1 | 11/2012 | Ullrich, Jr. et al. |
| 2012/0303129 A1 | 11/2012 | Bagga et al. |
| 2012/0310354 A1 | 12/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0316650 A1 | 12/2012 | Ullrich, Jr. et al. |
| 2012/0316651 A1 | 12/2012 | Ullrich, Jr. et al. |
| 2012/0316653 A1 | 12/2012 | Ullrich, Jr. et al. |
| 2013/0006363 A1 | 1/2013 | Ullrich, Jr. et al. |

FOREIGN PATENT DOCUMENTS

| | | |
|---|---|---|
| EP | 1449544 | 8/2004 |
| EP | 2 386 274 A1 | 11/2011 |
| JP | 08010276 | 1/1996 |
| JP | 19968010276 | 1/1996 |
| JP | 2001170092 | 6/2001 |
| WO | 9706753 | 2/1997 |
| WO | 98/01091 | 1/1998 |
| WO | 0128469 | 4/2001 |
| WO | 0170144 | 9/2001 |
| WO | 0195838 | 12/2001 |
| WO | 2004008983 | 1/2004 |
| WO | 2004041131 | 5/2004 |
| WO | 2006081843 | 8/2006 |
| WO | 2006116306 | 11/2006 |
| WO | 2006121795 | 11/2006 |
| WO | 2007089905 | 8/2007 |
| WO | 2008103843 | 8/2008 |
| WO | 2009006225 | 1/2009 |
| WO | 2009029458 | 3/2009 |
| WO | 2009129262 | 10/2009 |
| WO | 2009140544 | 11/2009 |
| WO | 2011094748 | 8/2011 |

OTHER PUBLICATIONS

Astra Tech Dental, "OsseoSpeed—more bone more rapidly", http://shop.dentsplyimplants.us, May 2011.

Guo, et al., "The effect of hydrofluoric acid treatment of TiO2 grit blasted titanium implants on adherent osteoblast gene expression in vitro and in vivo", Biomaterials 28 (Sep. 14, 2007) 5418-5425.

He, et al., "Mechanical and Histomorphometric Evaluations of Rough Titanium Implants Treated with Hydrofluoric Acid/Nitric Acid Solution in Rabbit Tibia", Int. J. Oral Maxillofac. Implants, Nov. 1, 2011; 26:115-122.

Isa, et al., "Effects of Fluoride-Modified Titanium Surfaces on Osteoblast Proliferation and Gene Expression", Int. J. Oral Maxillofac. Implants 2006; 21:203-211.

Lamolle, et al., "The effect of hydrofluoric acid treatment of titanium surface on nanostructural and chemical changes and the growth of MC3T3-E1 cells", Biomaterials 30 (Nov. 20, 2008) 736-742.

Meirelles, et al., "The Effect of Chemical and Nanotopographical Modifications on the Early Stages of Osseointegration", Int. J. Oral Maxillofac. Implants 2008; 23:641-647.

Supplementary Partial European Search Report issued Sep. 27, 2011.

Supplementary Partial European Search Report issued Aug. 19, 2011.

Variola, et al., "Nanoscale surface modifications of medically relevant metals: state-of-the art and prespectives", Nanoscale, 2011, 3, 335-353.

Wennerberg, et al., "Spontaneously formed nanostructures on titanium surfaces", Clin. Oral Impl. Res., 2012, 1-7.

Wennerberg, A., et al., "Effects of titanium surface topography on bone integration: a systematic review", Clin. Oral Impl. Res., 20 (Suppl. 4), 2009, pp. 172-184.

Pending U.S. Appl. No. 13/286,813 of Chad J. Patterson, et al. filed Nov. 1, 2011.

Pending U.S. Appl. No. 13/826,304 of Peter F. Ullrich, Jr., et al. filed Mar. 14, 2013.

Pending U.S. Appl. No. 13/713,417 of Chad J. Patterson, et al. filed Dec. 13, 2012.

Pending U.S. Appl. No. 13/784,144 of Peter F. Ullrich, Jr., et al. filed Mar. 4, 2013.

* cited by examiner

Ra = Average(1, 4, 6, 8, 5, 2, 1, 4, 1, 2, 1, 4, 7, 4, 1, 2, 5, 8, 2, 1, 4, 1, 1)

Ra = 3.26

Rpm = average(Rp1, Rp2, Rp3, ...)
Rvm = average(Rv1, Rv2, Rv3, ...)
RzDIN = Rtm = average(Rt1, Rt2, Rt3, ...)

Sm = average(S₁, S₂, S₃, ...)

PROCESSES FOR PRODUCING REGULAR REPEATING PATTERNS ON SURFACES OF INTERBODY DEVICES

CROSS REFERENCE TO RELATED APPLICATIONS

This application is a continuation-in-part of U.S. patent application Ser. No. 12/151,198, filed on May 5, 2008, and pending, which is a continuation-in-part of U.S. patent application Ser. No. 11/123,359, filed on May 6, 2005, and issued as U.S. Pat. No. 7,662,186. The contents of both prior applications are incorporated by reference into this document, in their entirety and for all purposes.

TECHNICAL FIELD

The present invention relates generally to improved processes of making interbody spinal implants and, more particularly, to processes of producing spinal implants having regular repeating patterns on integration surfaces of the implants.

BACKGROUND OF THE INVENTION

In the simplest terms, the spine is a column made of vertebrae and discs. The vertebrae provide the support and structure of the spine while the spinal discs, located between the vertebrae, act as cushions or "shock absorbers." These discs also contribute to the flexibility and motion of the spinal column. Over time, the discs may become diseased or infected, may develop deformities such as tears or cracks, or may simply lose structural integrity (e.g., the discs may bulge or flatten). Impaired discs can affect the anatomical functions of the vertebrae, due to the resultant lack of proper biomechanical support, and are often associated with chronic back pain.

Several surgical techniques have been developed to address spinal defects, such as disc degeneration and deformity. Spinal fusion has become a recognized surgical procedure for mitigating back pain by restoring biomechanical and anatomical integrity to the spine. Spinal fusion techniques involve the removal, or partial removal, of at least one intervertebral disc and preparation of the disc space for receiving an implant by shaping the exposed vertebral endplates. An implant is then inserted between the opposing endplates.

Spinal fusion procedures can be achieved using a posterior or an anterior approach, for example. Anterior interbody fusion procedures generally have the advantages of reduced operative times and reduced blood loss. Further, anterior procedures do not interfere with the posterior anatomic structure of the lumbar spine. Anterior procedures also minimize scarring within the spinal canal while still achieving improved fusion rates, which is advantageous from a structural and biomechanical perspective. These generally preferred anterior procedures are particularly advantageous in providing improved access to the disc space, and thus correspondingly better endplate preparation.

There are a number of problems, however, with traditional spinal implants including, but not limited to, improper seating of the implant, implant subsidence (defined as sinking or settling) into the softer cancellous bone of the vertebral body, poor biomechanical integrity of the endplates, damaging critical bone structures during or after implantation, and the like. In summary, at least ten, separate challenges can be identified as inherent in traditional anterior spinal fusion devices. Such challenges include: (1) end-plate preparation; (2) implant difficulty; (3) materials of construction; (4) implant expulsion; (5) implant subsidence; (6) insufficient room for bone graft; (7) stress shielding; (8) lack of implant incorporation with vertebral bone; (9) limitations on radiographic visualization; and (10) cost of manufacture and inventory.

With regard to manufacturing of such implants, there are traditionally many steps necessary to produce a high quality implant. For example, the manufacturing process may require a series of steps including, but not necessarily limited to, cutting the basic implant shape from raw materials and adding features by removing material from the initial basic shape. Conventional processes may include numerous steps of holding and releasing the part until the finished implant is completed. The part also may undergo subsequent surface processing to provide surface features on the completed implant—although certain surface features, such as grossly textured surfaces with undercuts or sharp edges, can work detrimentally in the healing process. In particular, undercuts or sharp edges can compound the load induced stresses imparted between the implant and the opposing bones, and the long term result can include degeneration of the bone structures.

SUMMARY OF THE INVENTION

The present invention provides for processes of producing interbody spinal implants having specifically designed surface features intended to influence the biological processes that occur during bone healing and fusion. In particular, the surface features of the implants may be produced by subtractive or additive processes that may be automated to produce desired surface patterns. In the case of a subtractive process, a mask may be used to provide the desired patterns and the automation provides for high mask location accuracy and uniform dispensing of the mask material. In the case of an additive process, the automation provides for uniform and accurate patterns applied to and protruding from the surface. In both cases, the implants have special surface features that may be produced rapidly with complex patterns designed to achieve a balanced surface having frictional characteristics and load dispersion over the cumulative surface area. The process also is designed so as not to constrain subsequent processes or degrade the previous process steps.

In one embodiment, the present invention provides a process of producing an interbody spinal implant having a regular repeating pattern including applying at least one additive process or subtractive process to at least one base surface of an interbody spinal implant to form a regular repeating pattern. The interbody spinal implant includes a body having a top surface, a bottom surface, opposing lateral sides, opposing anterior and posterior portions, a substantially hollow center, and a single vertical aperture; and optionally, at least one of a first integration plate affixed to the top surface of the body and a second integration plate affixed to the bottom surface of the body, where the first integration plate and the second integration plate each have a top surface, a bottom surface, opposing lateral sides, opposing anterior and posterior portions, and a single vertical aperture extending from the top surface to the bottom surface and aligning with the single vertical aperture of the body. In other words, the implant may comprise a solid-body implant or a composite structure.

The regular repeating pattern may be applied as an additive process or a subtractive process. In an additive process, a pattern is applied (e.g., an array of specs, dots, strips, or the like) to a base surface of the implant, for example, through deposition, welding, impacting, injection, or the like, to provide protrusions, extensions, or projections from the base surface. In a subtractive process, on the other hand, the pattern may be formed by making cuts, recesses, or removing portions of the base surface of the implant. For example, one or more patterns of maskant may be applied to the base surface (e.g., in an array of specs, dots, strips, or the like). Then, a chemical etchant (e.g., an acid etch) may be applied to remove the material in the regions not protected by the maskant to provide recesses, cuts, or holes in the base surface. The chemical etchant may be applied using any suitable technique (e.g., by spraying, immersion, or the like) to the unmasked surfaces. After etching, a single time or repeatedly, the maskant may then be removed to reveal the pattern. In both cases, complex patterns with highly accurate and specifically designed shapes may be obtained. The process may also include some combination of additive and subtractive techniques.

In another embodiment, a process of producing an interbody spinal implant having a regular repeating pattern includes obtaining an interbody spinal implant (e.g., by machining the implant from a blank or raw material) and repeatedly (e.g., more than once) applying an additive process to at least one base surface of the interbody spinal implant to form a roughened surface topography having a regular repeating pattern. The additive process (e.g., deposition) may be applied sequentially, for example, to provide an array of shapes or structures protruding from the base surface.

In another embodiment, a process of producing an interbody spinal implant having a regular repeating pattern includes obtaining an interbody spinal implant and repeatedly applying a subtractive process to at least one base surface of the interbody spinal implant to form a roughened surface topography having a regular repeating pattern. The repeated process may include, for example, applying a first maskant; then applying a first chemical etchant; subsequently applying a second maskant; and then applying a second chemical etchant, in a repeated manner. Alternatively, the process may include applying a first maskant, applying a second maskant, and so on; and then applying a first chemical etchant, optionally, applying a second chemical etchant, and so on. The subtractive process (e.g., acid etching) may be applied sequentially, for example, to provide an array of shapes or structures recessed into the base surface.

The regular repeating pattern in the subtractive or additive processes may form a roughened surface topography. The roughened surface topography may help to promote bone growth, fusion, and healing responses and may be oriented in opposition to the biologic forces on the interbody spinal implant and to an insertion direction.

The regular repeating pattern may be applied to at least one surface of the implant. Preferably, the pattern is applied to the integration surface or surfaces of the implant. In the case of a solid-body implant, the integration surface includes the top surface, bottom surface, or both surfaces of the implant. In the case of a composite implant with a single integration plate, the integration surfaces include the top surface of the integration plate and the top surface of the body of the implant or the top surface of the integration plate and the bottom surface of the body of the implant. In the case of a composite implant with two integration plates, the integration surface may include the top surface of both integration plates (i.e., the outer surfaces).

The resulting implant, for a solid-body implant or a composite implant, comprises at least one integration surface having a roughened surface topography where the entire implant or the integration plate was produced by such a process that at least the integration surfaces of the implant comprise a selective pattern of high accuracy.

Various implant body shapes are provided to allow for implantation through various access paths to the spine through a patient's body. The structures and surfaces are designed to work in concert to preserve endplate bone structures, provide for sufficient bioactivity in each respective location, and provide stability within the disc space and the graft containment axial column. In particular, the shapes and textures of the bioactive surfaces vary based on the implant insertion path, location within the disc space, and frictional characteristics of the surfaces.

BRIEF DESCRIPTION OF THE DRAWING

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following figures.

DETAILED DESCRIPTION OF THE INVENTION

Figure 1:
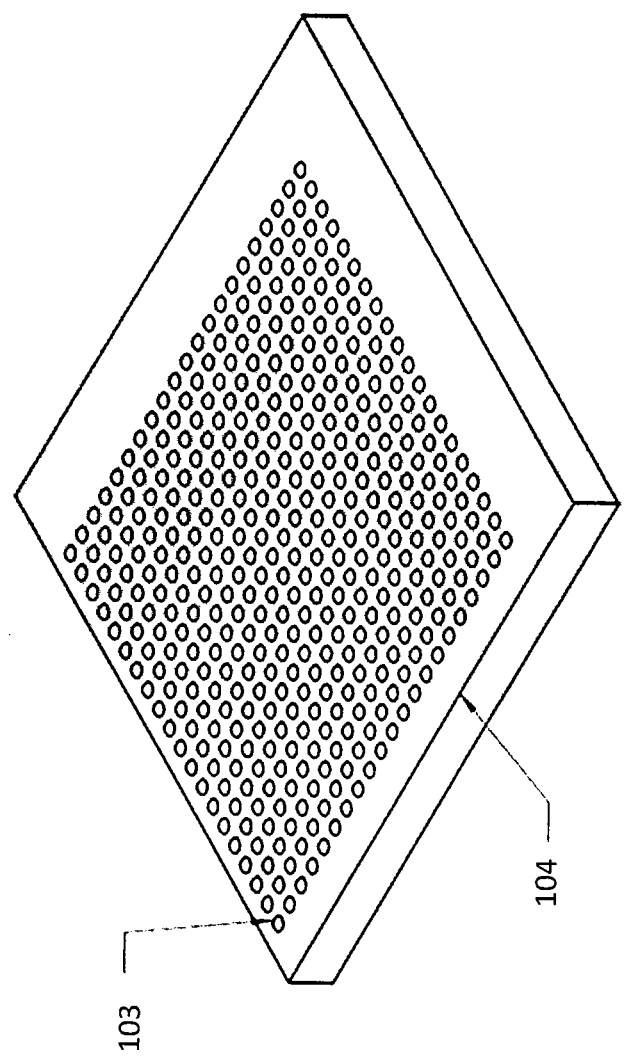
FIG. 1 shows an example of a first step of a subtractive process where rows of maskant are applied in an array to a surface of an implant.

The present invention provides for interbody spinal implants, including solid-body implants and composite implants, having surfaces with a specific pattern designed to influence, for example, healing and fusion responses and provide a balanced friction inducing load dispersing surface.

Accordingly, in one embodiment of the present invention, a process of producing an interbody spinal implant includes applying at least one additive process or subtractive process to at least one base surface of an interbody spinal implant to form a regular repeating pattern (e.g., a roughened surface topography).

The implant may be obtained or produced, for example, by machining the implant from a raw material, and once the implant is produced, then applying surface processing to the surfaces requiring such treatment. For example, the raw material may be obtained from a supplier, and machined (e.g., milled or turned) into the basic implant shape and having certain features (e.g., apertures). After machining the implant, certain surface features may be applied to desired surfaces. For example, a protective maskant may be applied to protect the surfaces of the implant where those protected surfaces will not undergo any surface treatment. The protective mask may be applied to the entire implant (e.g., by immersion in the maskant) or a portion of the implant. Then, a portion of the protective mask may be removed to expose the area of the implant which requires a special surface treatment (e.g., the integration surfaces). A protective maskant may or may not be required depending on the process employed.

Creating the Pattern

Once the given area of the surface is prepared (e.g., exposed and unmasked) for a surface treatment, at least one additive process or subtractive process may be applied to the base surface. As used in this document, the "base surface" includes the original surface of the implant. In other words, the base surface includes any of the surfaces which define the implant before undergoing surface processing. The base surface may also include, however, a modified original surface, for example, a base surface that has previously undergone at least one subtractive process, additive process, or both processes (e.g., exposing new surfaces from the original surface or providing new surfaces on to the original surface).

The shapes of the frictional surface protrusions or recesses provided by the subtractive process, additive process, or both processes form a roughened surface topography on at least one surface of the implant. The roughened surface topography preferably includes a predetermined repeating pattern. As used in this document, "predetermined" means determined beforehand, so that the predetermined characteristic must be determined, i.e., chosen or at least known, before use of the implant. The pattern may consist of an array of shapes or structures. The array may include a systematic arrangement of objects (e.g., dots, circles, ovals, squares, or strips) in rows, columns, or both.

The shapes may be formed using processes and methods commonly applied to remove material (e.g., subtractive techniques) during fabrication of implantable devices such as cutting and removal processes, machining, chemical etching, abrasive media blasting, and others known in the art. Alternatively or in addition, the shapes may be formed using methods commonly applied to add material (e.g., additive processes) to a surface such as coating, sputtering, printing, and other additive processes known in the art.

(a) Subtractive Process

A subtractive process may be applied to at least one surface of the implant. As used in this document, "subtractive process" is intended to encompass any process which removes material (e.g., metal or plastic) from a surface of the implant. Suitable subtractive techniques may include, but are not limited to, machining (e.g., milling, turning, or both techniques may be performed using machine tools, such as saws, lathes, milling machines, drill presses, or other equipment used with a sharp cutting tool to physically remove material to achieve a desired geometry); unmasked or masked etching (e.g., portions of the surface are protected by a masking material which resists etching and an etching substance is applied to unmasked portions); chemical, photo, electrical, electrochemical, plasma, or laser etching; cutting and removal processes; casting; forging; machining; drilling; grinding; shot peening; abrasive media blasting (such as sand or grit blasting); and combinations of these subtractive processes.

The subtractive process may include applying a temporary patterned mask before the subtractive process is performed. In other words, a mask may be applied to the desired surface, for example, to produce a desired pattern before implementing the subtractive technique. The pattern may include a designed configuration or array of dots, circles, semi-circles, squares, triangles, lines, strips, amorphous shapes, or any suitable pattern designed to provide frictional contact with opposing bones, dispersion loading, and to promote bone healing and fusion. Referring to the drawing, in which like reference numbers refer to like elements throughout the various figures that comprise the drawing, FIG. 1 depicts an embodiment of the invention where rows of maskant are applied in a first pattern 103 (e.g., dots or circles) on an original surface 104 of the implant 1.

The maskant may be applied using any suitable techniques known in the art, such as deposition (e.g., sputter deposition, vacuum deposition, physical vapor deposition, chemical vapor deposition, and spin coating), evaporation (e.g., electron beam evaporation, thermal evaporation, and plasma assisted thermal evaporation), and the like. The sputtering may include, for example, DC sputtering, DC magnetron sputtering, AC sputtering, pulse DC sputtering, RF sputtering, etc. In an exemplary embodiment, the maskant is applied automatically in a regular repeating pattern (e.g., an array) using a sputtering technique. Preferably, the maskant is applied automatically using an ink jet printing apparatus or system (e.g., digital ink jet technology). For example, a moving injector may pass rapidly over the surface and dispense (e.g., under pressure) small amounts of the maskant onto the surface in the pattern. As shown in FIG. 1, an array of maskant may be applied in a first pattern 103, for example, by a printing system.

A suitable maskant may be selected by one of ordinary skill in the art depending on the subtractive process employed. The maskant may include, for example, polymeric masks or inorganic masks (e.g., $SiO_2$, W, hydrogen silsesquioxane). The mask may also include photosensitive masks. If necessary, the mask may be cured, for example, at room temperature or under heating before applying the subtractive process (e.g., acid etching). Preferably, the maskant should be selected to be able to withstand the subtractive process and any further processing of the implant.

The subtractive process may include a single subtractive step or multiple subtractive steps. The subtractive process may be applied sequentially, for example, to provide an array of shapes or structures recessed into the base surface. In an exemplary embodiment, the process is repeated (occurs more than once) and may include, for example, (1) applying a first maskant and then applying a first chemical etchant; and (2) subsequently applying a second maskant and then applying a second chemical etchant. Steps (1) and (2) may continue repeatedly until the desired pattern is obtained. In the alternative or in addition, the process may include, for example, (1) applying a first maskant, applying a second maskant, and applying as many additional masks as are necessary to produce the desired pattern; and (2) then applying a first chemical etchant, optionally, applying a second chemical etchant, and so on to produce the required degree of etching.

Figure 2:
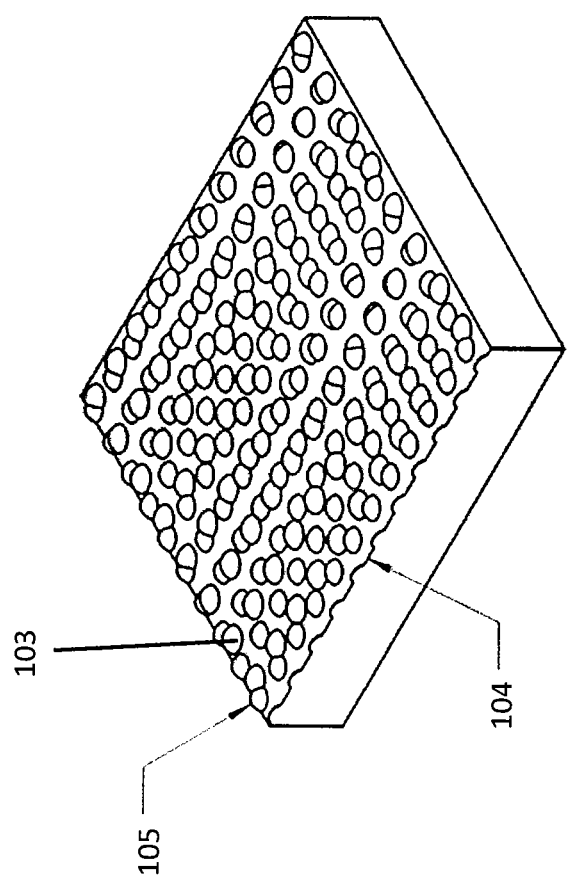
FIG. 2 shows an example of a second step of the subtractive process where a second overlapping layer of maskant is applied to the surface of the implant shown in FIG. 1.
Figure 3:
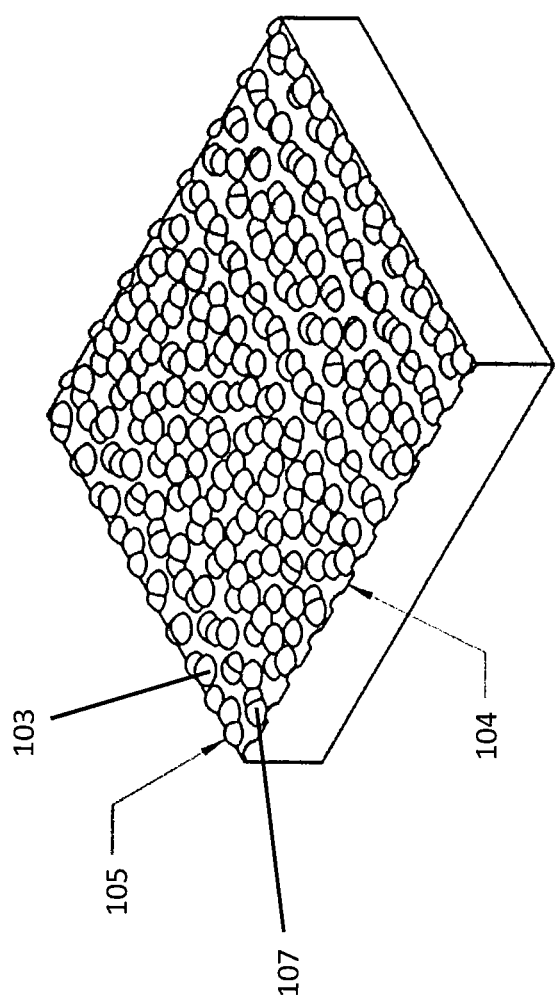
FIG. 3 shows an example of a third step of the subtractive process where a third overlapping layer of maskant is applied to the surface of the implant shown in FIG. 2.

FIGS. 1-3 show an example of a three step process of applying maskant to an original surface 104 of an implant. In a first step shown in FIG. 1, an array of maskant is applied in a first pattern 103 (e.g., dots or circles) on an original surface 104 of the implant 1. In a second step shown in FIG. 2, another layer of maskant is applied in a second pattern 105 (e.g., dots or circles) at least partially overlapping the first pattern 103. In a third step shown in FIG. 3, another layer of maskant is applied in a third pattern 107 (e.g., dots or circles) at least partially overlapping the first pattern 103, the second pattern 105, or both patterns. More layers of maskant may be applied if necessary to form the desired pattern. After the pattern of maskant is applied to the original surface, then a chemical etchant may be applied to the portions of the original surface that are unprotected by maskant. For example, the surface may be subjected to acid etching, with a strong acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The acid etching may also be repeated, if desired, to obtain the predetermined pattern of recesses.

Figure 4A:
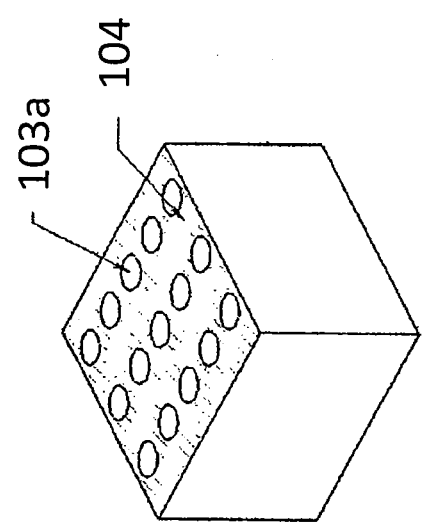
FIGS. 4A-4C show an example of a pattern of cuts formed by a three step process in the surface of the implant.
Figure 4B:
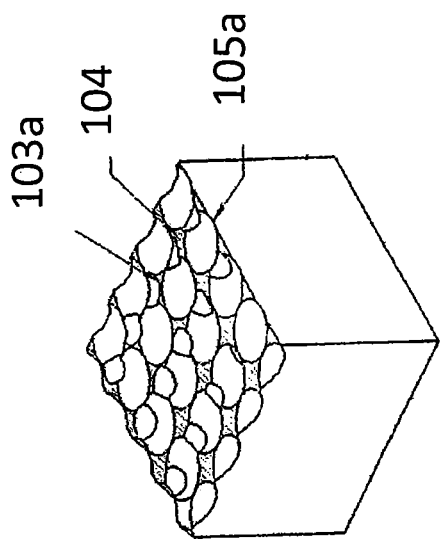
Figure 4C:
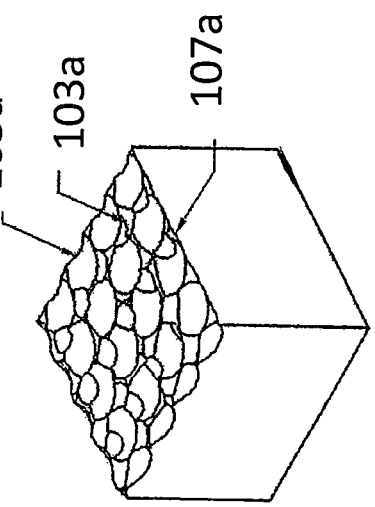
Figure 5:
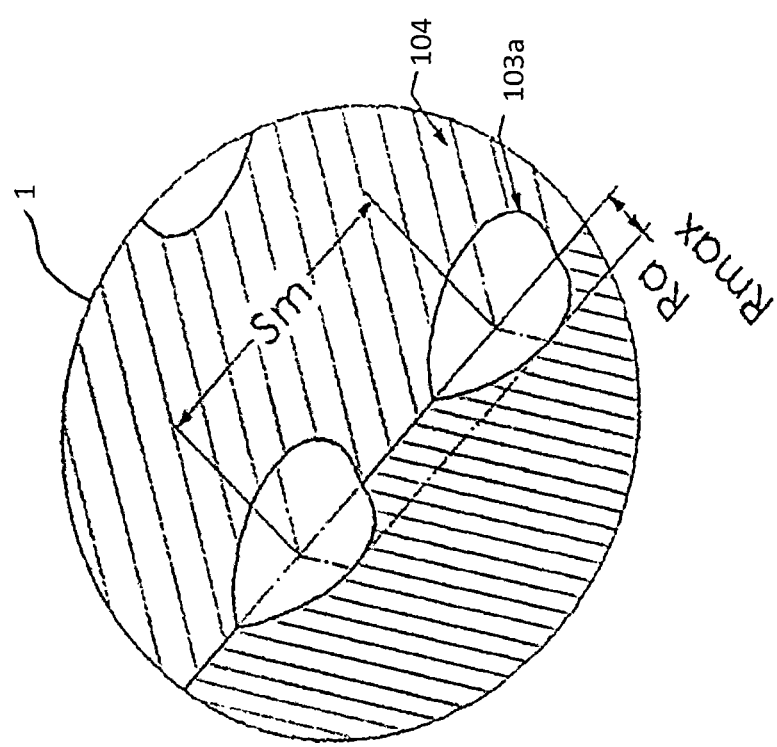
FIG. 5 shows Ra, Rmax, and Sm for a roughened surface topography.

FIGS. 4A-4C depict an alternative embodiment where the pattern array is directly cut, for example, by etching. Therefore, a mask may be applied to areas of the original surface which are not part of the cut pattern. In a three-step process, for example, the subtractive process may form a first cut pattern 103a, second cut pattern 105a, and third cut pattern 107a, respectively.

Figure 6:
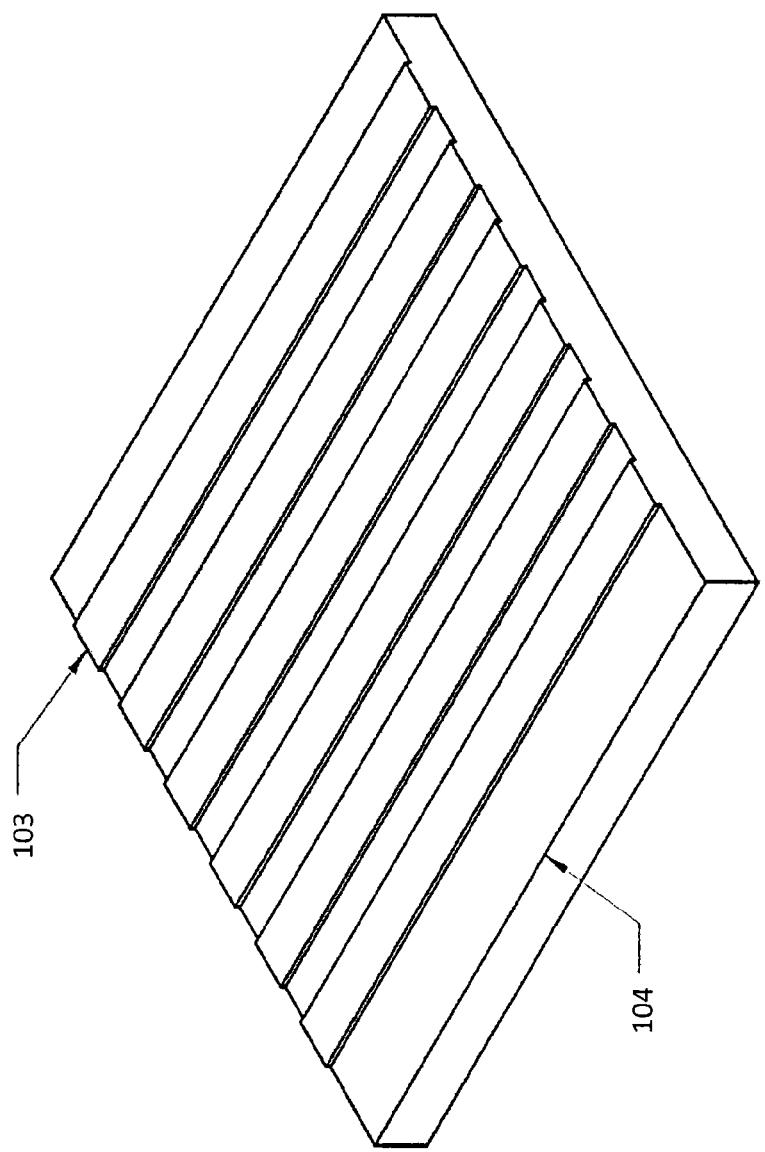
FIG. 6 shows an example of a first step of a subtractive process where strips of maskant are applied to a surface of the implant.
Figure 7:
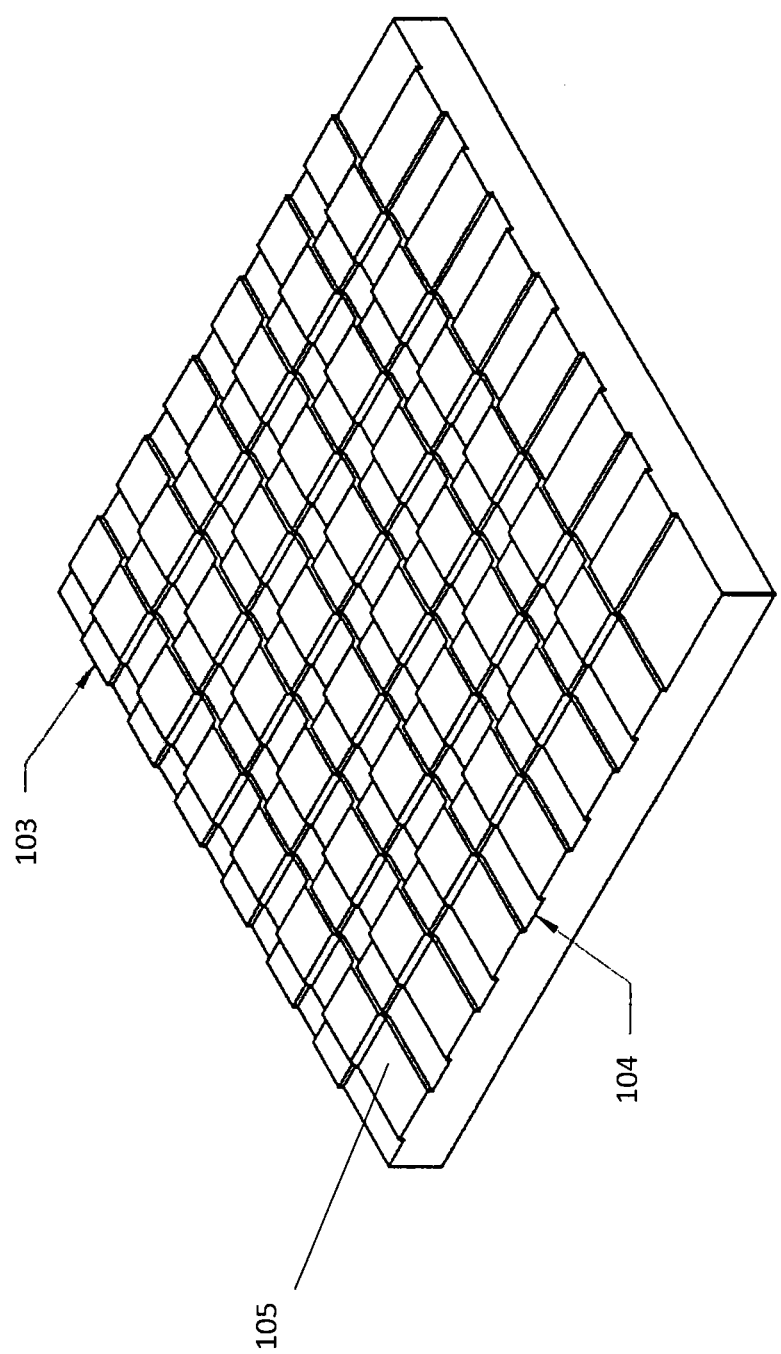
FIG. 7 shows an example of a second step of the subtractive process where overlapping strips of maskant are applied to the surface of the implant shown in FIG. 6.

FIGS. 6 and 7 depict an alternative embodiment where the first pattern 103 includes rows of maskant applied in a pattern of strips on the original surface 104. The strips of maskant are applied in a series of equal parallel intervals. Then, a second pattern 105, also applied as strips of maskant in a series of equal parallel intervals, is aligned perpendicularly to the first pattern 103, for example, to form a lattice or basket pattern. It is also envisioned that other angles (e.g., between 0° and 90°) may be produced in the overlapping patterns. After the pattern of maskant is applied, then an etchant may be applied, for example, to the portions of the original surface that are unprotected by the maskant.

Once the subtractive process is complete and the pattern has been formed and cut into the implant, any mask used in the process may be removed using suitable mechanisms known in the art. For example, the mask may be peeled or scraped, removed by a solvent or heat, dissolved by light, etc.

(b) Additive Process

An additive process may be applied to at least one surface of the implant. As used in this document, "additive process" is intended to encompass any process which adds material to a surface of the implant. The additive process may form protrusions, projections, extensions, or the like extending outwardly from the base surface in a three dimensional manner. Preferably, however, the added features do not comprise teeth or other sharp projections. Suitable additive techniques may include, but are not limited to, sputtering, printing, welding, coating, depositing molten material, impacting, injecting, optical melt additive processes, and other additive processes known in the art. Additive processes typically do not require a maskant to be applied to form a pattern, but a mask may be applied, for example, to protect certain surfaces.

Figure 8:
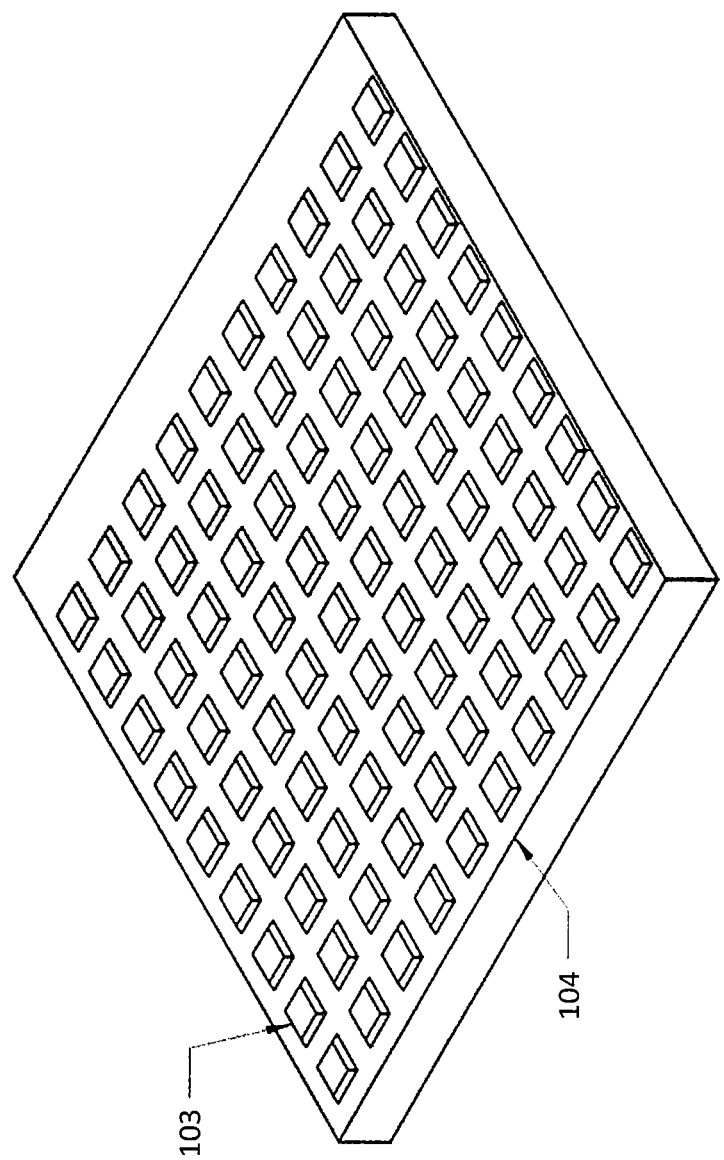
FIG. 8 shows an example of an additive process where a patterned array of squares is applied to the surface of the implant.

The additive process may include applying the pattern directly to the surface. The pattern may include a designed configuration or array of lines, strips, dots, spherical shapes (e.g., spheres, semi-spheres), quadrilateral shapes (e.g., cubes, polyhedral pyramids), or amorphous or irregular shapes including any suitable pattern designed to provide frictional contact with opposing bones, dispersion loading, and to promote bone healing and fusion. FIG. 8 depicts an embodiment of the invention where protruding rows of material are applied in a first pattern 103 (e.g., squares or cubes) on an original surface 104 of the implant 1.

The pattern may be applied using any suitable techniques known in the art, such as deposition (e.g., sputter deposition, vacuum deposition, physical vapor deposition, chemical vapor deposition, and spin coating), evaporation (e.g., electron beam evaporation, thermal evaporation, and plasma assisted thermal evaporation), and the like. The sputtering may include, for example, DC sputtering, DC magnetron sputtering, AC sputtering, pulse DC sputtering, RF sputtering, etc. In an exemplary embodiment, the pattern is automatically applied to the surface in a regular repeating pattern (e.g., an array) using a sputtering technique. Preferably, the pattern is directly applied to the surface using an ink jet printing apparatus. As shown in FIG. 8, an array of material may be applied in a first pattern 103, for example, by a printing system.

The additive features may contain any suitable material, which may be the same or a different material then the surface being treated. Suitable materials may be selected by one of ordinary skill in the art depending on the additive process employed. The material may include, for example, polymeric or inorganic materials (e.g., titanium) including any of the materials used to form the implant 1. The added material may be selected to be able to withstand any further processing of the implant. It may also be desired, however, that the added material is at least partially removed by subtractive techniques. In one embodiment, the surface undergoes an additive process and a subtractive process (e.g., etching) which removes at least a portion of the features added in the additive process.

The additive process may include a single additive step or multiple additive steps. The additive process may be applied sequentially, for example, to provide an array of shapes or structures protruding from the base surface. In an exemplary embodiment, the process is repeated (occurs more than once) and may include, for example, applying a first pattern of protrusions and then applying a second pattern of protrusions. In another embodiment, the process includes applying a first pattern of protrusions and then applying a pattern of recesses using a subtractive process.

Figure 9:
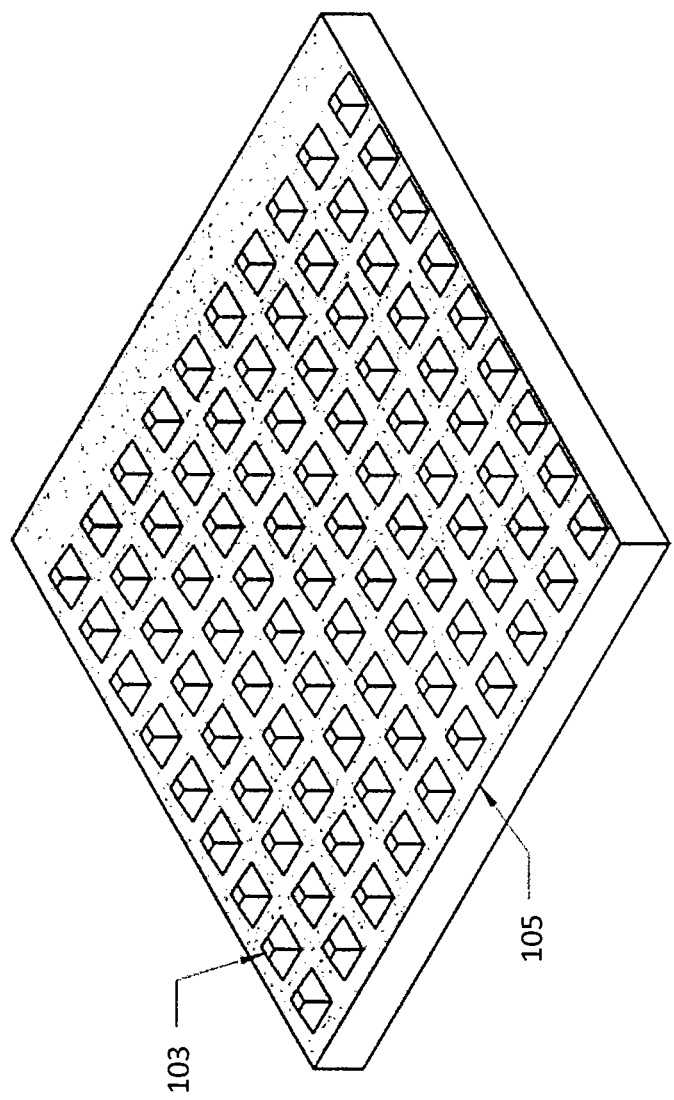
FIG. 9 shows an example of a surface of the implant following two additive processes with a patterned array.

FIG. 9 shows an example of a two-step additive process on a surface of the implant 1. In a first step, a first pattern 103 is applied in an array of protruding squares or cubes on the original surface 104 of the implant 1. In a second step, a second pattern 105 of dots is applied to the areas not covered by the first pattern 103. In the alternative, the second pattern 105 may also at least partially overlap the first pattern 103.

Figure 10:
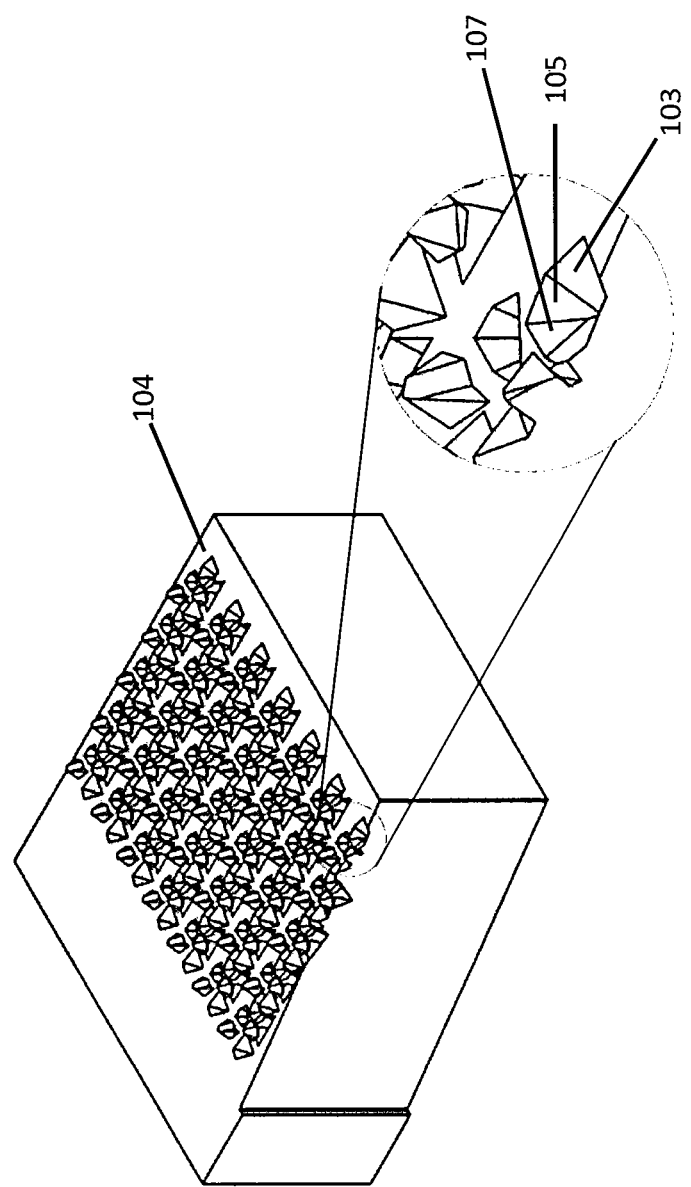
FIG. 10 shows an example of an abraded surface detail that may be produced by an additive or subtractive process.

FIG. 10 shows an alternative example depicting an abraded surface detail which may be produced in an additive process, a subtractive process, or both processes. The three patterns may be applied simultaneously or sequentially to form a first pattern 103, a second pattern 105, and a third pattern 107 recessed into or projecting from the original surface 104. For example, the three patterns may form an overall repeating pattern on the surface of the implant 1.

Surface Topography

The subtractive process, additive process, or both processes may form a roughened surface topography 80 from macro processing, micro processing, nano processing, or any combination of the three. The term "macro" typically means relatively large; for example, in the present application, dimensions measured in millimeters (mm). The term "micro" typically means one millionth ($10^6$); for example, in the present application, dimensions measured in microns (μm) which correspond to $10^{-6}$ meters. The term "nano" typically means one billionth ($10^{-9}$); for example, in the present application, dimensions measured in nanometers (nm) which correspond to $10^{-9}$ meters.

Figure 18:
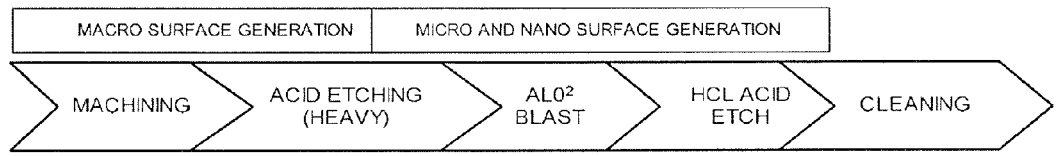
FIG. 18 illustrates one set of process steps that can be used to form macro, micro, or nano processes.

FIG. 18 illustrates one set of process steps that can be used to form macro, micro, or nano processes. As illustrated, there may be some overlap in the processes that can be applied to form each of the three types of features (macro, micro, and nano). For example, acid etching can be used to form the macro features, then the same or a different acid etching process can be used to form the micro features. The features may be provided in a random design or a predetermined pattern (e.g., a repeating pattern).

(a) Macro Features

The macro features of the roughened surface topography 80 are relatively large features (e.g., on the order of millimeters). The macro features may be formed from subtractive techniques (e.g., mechanical or chemical bulk removal, for example) or additive techniques (e.g., deposition or sputtering) as described above. The patterns may be organized in regular repeating patterns and optionally overlapping each other. In one embodiment, the macro features may be formed in three, sequential steps.

FIG. 4A illustrates the result of one step or a first step in forming macro features. Specifically, a first cut pattern 103a of the macro features is formed in a surface (e.g., the top surface 81 of an integration plate 82). The "cut 1" features of the first cut pattern 103a may cover about 20% of the total area of the surface, for example, leaving about 80% of the original surface 104 remaining. The range of these percentages may be about ±20%, preferably ±10%, and more preferably about ±5%. The "cut 1" features of the first cut pattern 103a do not have any undercuts. In one embodiment, these "cut 1" features have the smallest diameter and greatest depth of the macro features that are formed during the sequential steps.

FIG. 4B illustrates the result of a second step in forming macro features. Specifically, a second cut pattern 105a of the macro features is formed in the surface. Together, the "cut 1" features of the first cut pattern 103a and the "cut 2" features of the second cut pattern 105a may cover about 85% of the total area of the surface, for example, leaving about 15% of the original surface 104 remaining. The range of these percentages may be about ±10% and preferably ±5%. In an embodiment of the invention, these "cut 2" features have both a diameter and a depth between those of the "cut 1" and "cut 3" features of the macro features that are formed during the first and third steps of the process of trimming the macro features of the roughened surface topography 80.

FIG. 4C illustrates the result of the third step in forming macro features. Specifically, a third cut pattern 107a of the macro features may be formed in the surface. Together, the "cut 1" features of the first cut pattern 103a, the "cut 2" features of the second cut pattern 105a, and the "cut 3" features of the third cut pattern 107a cover about 95% of the total area of the surface, for example, leaving about 5% of the original surface 104 remaining. The range of these percentages may be about ±1%. In an embodiment of the invention, these "cut 3" features may have the largest diameter and least depth of the macro features that are formed during the sequential process steps. Following completion of the three, sequential processing steps, the finished macro features may comprise multiple patterns of the three, overlapping cuts: the first cut pattern 103a, the second cut pattern 105a, and the third cut pattern 107a.

(b) Micro Features

The micro features may also be formed from subtractive techniques (e.g., mechanical or chemical bulk removal, for example) or additive techniques (e.g., deposition or sputtering) described above.

In an exemplary embodiment, the micro features are removed by masked or unmasked etching, such as acid etching. For example, portions of the surface may be exposed to a chemical etching. In an exemplary embodiment, the micro process includes an acid etching, with a strong acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The etching process may be repeated a number of times as necessitated by the amount and nature of the irregularities required for any particular application. Control of the strength of the etchant material, the temperature at which the etching process takes place, and the time allotted for the etching process allow fine control over the resulting surface produced by the process. The number of repetitions of the etching process can also be used to control the surface features. For example, the roughened surface topography 80 may be obtained via the repetitive masking and chemical or electrochemical milling processes described in U.S. Pat. Nos. 5,258,098; 5,507,815; 5,922,029; and 6,193,762, the contents of which are incorporated by reference into this document, in their entirety, and for all purposes.

By way of example, an etchant mixture of at least one of nitric acid and hydrofluoric acid may be repeatedly applied to a titanium surface to produce an average etch depth of about 0.53 mm. In another example, chemical modification of a titanium surface can be achieved using at least one of hydrofluoric acid, hydrochloric acid, and sulfuric acid. In a dual acid etching process, for example, the first exposure is to hydrofluoric acid and the second is to a hydrochloric acid and sulfuric acid mixture. Chemical acid etching alone may enhance osteointegration without adding particulate matter (e.g., hydroxyapatite) or embedding surface contaminants (e.g., grit particles).

The micro features may also be created by abrasive or grit blasting, for example, by applying a stream of abrasive material (such as alumina, sand, and the like) to the surface. In an exemplary embodiment, the micro features are created, at least partially, with an aqueous hydrochloric acid etching step and at least partially with an $AlO_2$ blasting step. Patterns may be organized in regular repeating patterns and optionally overlapping each other. After the micro features are formed, it is possible that less than about 3% of the original surface 104 remains. The range of that percentage may be about ±1%.

(c) Nano Features

The nano features may also be formed from subtractive techniques (e.g., mechanical or chemical bulk removal, for example) or additive techniques (e.g., deposition or sputtering) described above.

In an exemplary embodiment, the nano features are removed by masked or unmasked etching. For example, portions of the surface, optionally including portions of the surface exposed by the macro and micro steps described above, may be exposed to a chemical etching. In an exemplary embodiment, the nano process also includes an acid etching, with a strong or weak acid, such as hydrochloric acid (HCl), hydroiodic acid (HI), hydrobromic acid (HBr), hydrofluoric (HF), perchloric acid ($HClO_4$), nitric acid ($HNO_3$), sulfuric acid ($H_2SO_4$), and the like. The acid etching process for the nano step is preferably less aggressive than the acid etching process in the micro step. In other words, a less acidic, milder, or more diluted acid may be selected. In an exemplary embodiment, the nano features are created, at least partially, with an aqueous hydrochloric acid etching step.

The acid solution may be prepared using any suitable techniques known in the art. For example, the acid solution may be prepared by combining hydrochloric acid and water, simultaneously or sequentially. The acid solution may be applied to the implant 1 using any suitable mechanism or techniques known in the art, for example, immersion, spraying, brushing, and the like. If desired, certain areas of the implant 1 may be masked in patterns or to protect certain portions of the implant 1. After the acid solution is applied, the acid solution may be removed, for example, by rinsing with water (e.g., deionized water).

It is contemplated that the nano features may also be created by the abrasive or grit blasting, for example, described for the micro processing step. Patterns may be organized in regular repeating patterns and optionally overlapping each other. The nano features may also be achieved by tumble finishing (e.g., tumbling) the part or the implant 1. Suitable equipment and techniques can be selected by one of ordinary skill in the art. For example, a barrel may be filled with the parts or implants 1 and the barrel is then rotated. Thus, the part or implants 1 may be tumbled against themselves or with steel balls, shot, rounded-end pins, ballcones, or the like. The tumbling process may be wet (e.g., with a lubricant) or dry. After the nano features are formed, it is possible that less than about 1% of the original surface 104 remains. For example, after the nano features are formed, the roughened surface topography 80 may cover substantially the entire surface.

As should be readily apparent to a skilled artisan, the processes described in this document can be adjusted to create a mixture of depths, diameters, feature sizes, and other geometries suitable for a particular implant application. The orientation of the pattern of features can also be adjusted. Such flexibility is desirable, especially because the ultimate pattern of the roughened surface topography 80 should be oriented in opposition to the biologic forces on the implant 1 and to the insertion direction. In one particular embodiment, for example, the pattern of the roughened surface topography 80 may be modeled after an S-shaped tire tread.

The subtractive process and the additive process form a roughened surface topography 80. The resulting surfaces preferably have repeating patterns in the shape and location of the features. These patterns allow for the design and production of surfaces that resist motion induced by loading in specific directions that are beneficial to the installation process and resist the opposing forces that can be the result of biologic or patient activities such as standing, bending, or turning or as a result of other activities. The shapes of the surface features work to increase the surface contact area but do not result in undercuts that generate a cutting or aggressively abrasive action on the contacting bone surfaces.

Integration Surface

In an exemplary embodiment, the subtractive or additive process is applied to at least one of the surfaces which form the integration surfaces of the implant. As used in this document, the integration surface is the surface at least partially in contact with the vertebral or bone structure. In particular, the subtractive or additive process may be applied to the top surface of the implant, the bottom surface of the implant, or both surfaces. The subtractive or additive process may be applied to the entire surface or a portion of the integration surface.

The integration surfaces on the implant preferably have predefined surface features that (a) engage the vertebral endplates with a friction fit and, following an endplate preserving surgical technique, (b) attain initial stabilization, and (c) benefit fusion. The composition of the endplate is a thin layer of notch-sensitive bone that is easily damaged by features (such as teeth) that protrude sharply from the surface of traditional implants. Avoiding such teeth and the attendant risk of damage, the roughened surface topography 80 of the integration surface(s) does not have teeth or other sharp, potentially damaging structures; rather, the roughened surface topography 80 may have a pattern of repeating features of predetermined sizes, smooth shapes, and orientations.

These designed surfaces are composed of various sizes of features that, at the microscopic level, interact with the tissues and stimulate their natural remodeling and growth. At a larger scale these features perform the function of generating non-stressful friction that, when combined with a surgical technique that retains the most rigid cortical bone structures in the disc space, allows for a friction fit that does not abrade, chip, perforate, or compromise the critical endplate structures. The features may be divided into three size scales: nano, micro, and macro. The overlapping of the three feature sizes can be achieved using manufacturing processes that are completed sequentially and, therefore, do not remove or degrade the previous process.

Implant Structure

Figure 11A:
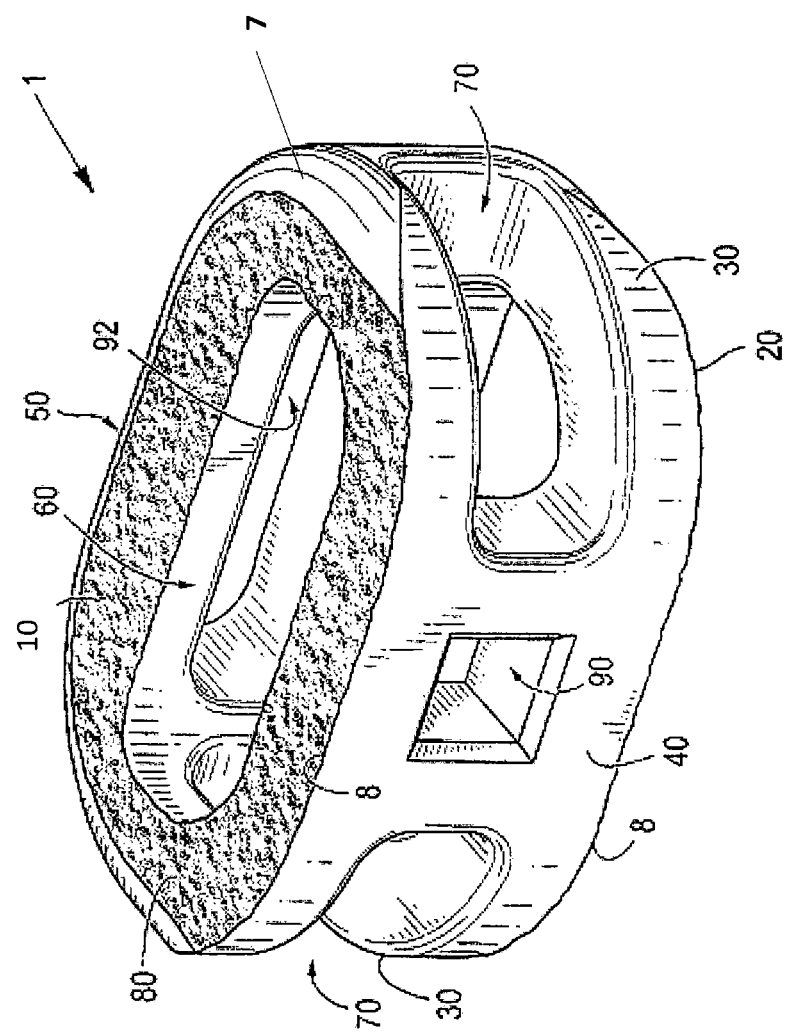
FIG. 11A shows a perspective view of an embodiment of the interbody spinal implant having a generally oval shape and roughened surface topography on the top surface.
Figure 11B:
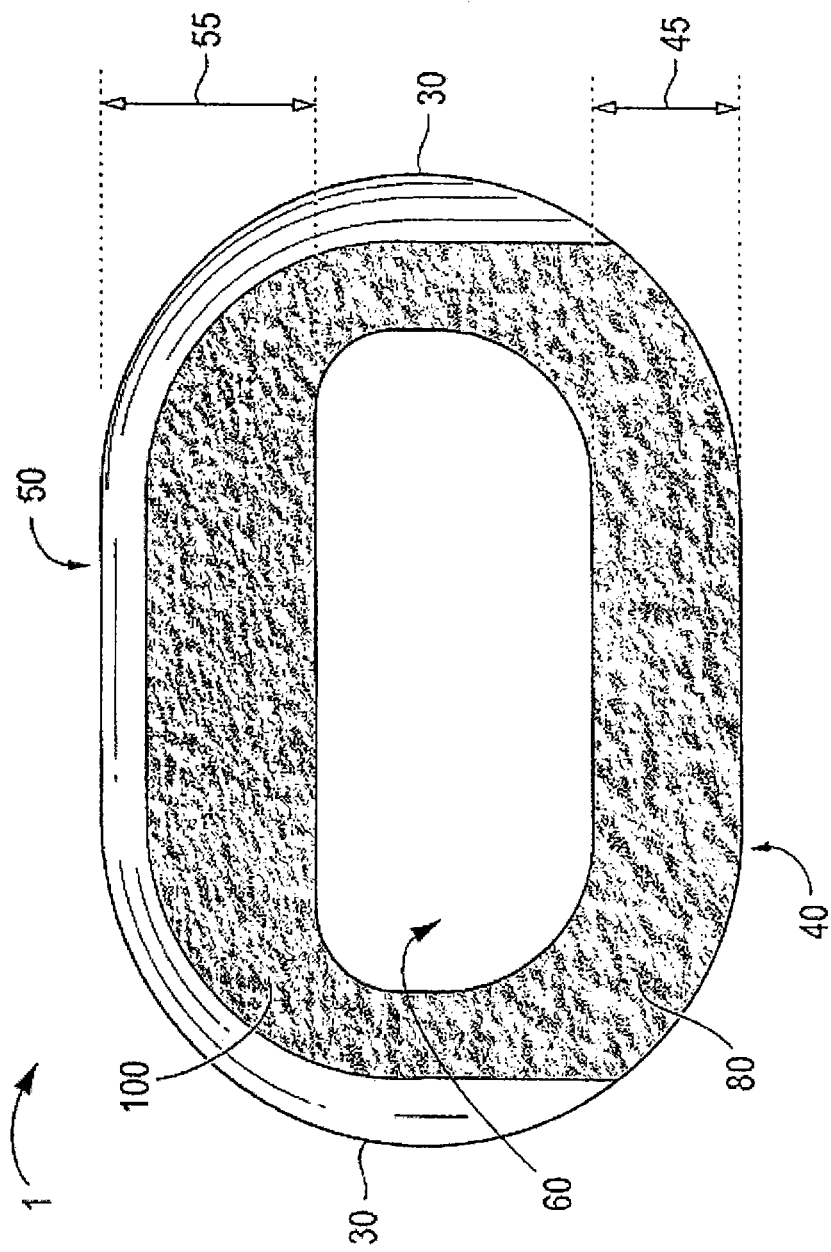
FIG. 11B shows a top view of the embodiment of the interbody spinal implant illustrated in FIG. 11A.

FIG. 11A shows a perspective view of an interbody spinal implant 1, which is especially well adapted for use in an Anterior Lumbar Interbody Fusion (ALIF) procedure. The interbody spinal implant 1 includes a top surface 10, a bottom surface 20, opposing lateral sides 30, and opposing anterior 40 and posterior 50 portions. The interbody spinal implant 1 may include implants made of a single piece of material or composite implants.

Interbody spinal implants 1 made of a single piece of material or solid-body implants do not include integration plates 82. The integration surface may include the top surface 10 of the implant 1, the bottom surface 20 of the implant 1, or both surfaces. The integration surface has a roughened surface topography 80, without sharp teeth that risk damage to bone structures, which was formed in the subtractive process or additive process described above.

Figure 12:
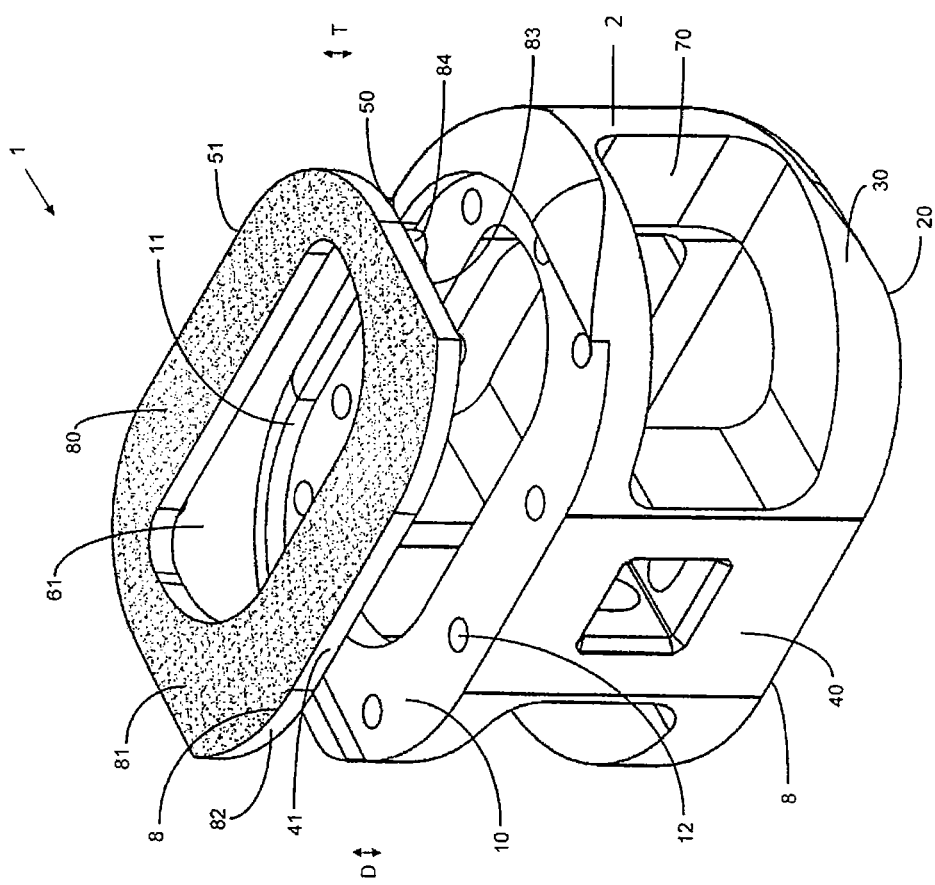
FIG. 12 shows an exploded view of a generally oval-shaped implant with an integration plate.

Composite implants include at least a body 2 and one or two integration plates 82, which may be formed from the same or different materials. As depicted in FIG. 12, the implant 1 includes a first integration plate 82 affixed to the top surface 10 of the body 2 and an optional second integration plate 82 (shown in FIG. 13) affixed to the bottom surface 20 of the body 2. The first integration plate 82 and optional second integration plate 82 each have a top surface 81, a bottom surface 83, opposing lateral sides, opposing anterior portion 41 and posterior portion 51, and a single vertical aperture 61 extending from the top surface 81 to the bottom surface 83 and aligning with the single vertical aperture 60 of the body 2.

When present, the integration plate(s) 82 comprise an integration surface (e.g., the top surface 81 of the integration plate 82), which is adapted to grip bone through friction generated when the implant 1 is placed between two vertebrae and to inhibit migration of the implant 1 once implanted. The integration surfaces may also have a fusion and biologically active surface geometry. In other words, at least a portion of the top surface 81 of the first integration plate 82 (e.g., a first integration surface) and optionally a top surface 81 of a second integration plate 82 (e.g., a second integration surface) has a roughened surface topography 80, without sharp teeth that risk damage to bone structures. The roughened surface topography 80 preferably includes micro features of a regular repeating pattern, formed during the subtractive or additive process, which may promote biological and chemical attachment or fusion with the bone structure.

The body 2 and at least one integration plate 82 are preferably compatibly shaped, such that the implant 1 having the body 2 and integration plate(s) 82 joined together may have a generally oval shape, a generally rectangular shape, a generally curved shape, or any other shape described or exemplified in this specification. Thus, for example, the body 2 and the integration plate(s) 82 may be generally oval-shaped in transverse cross-section. The body 2 and the integration plate(s) 82 may be generally rectangular-shaped in transverse cross-section. The body 2 and the integration plate(s) 82 may be generally curved-shaped in transverse cross-section.

The body 2 and integration plate(s) 82 of the implant 1 may be the same material or may be different. The body 2 and the integration plate(s) 82 may be composed of a suitable biocompatible material. In an exemplary embodiment, the body 2 and optional integration plate(s) 82 are formed of metal, which may be coated or not coated. Suitable metals, such as titanium, aluminum, vanadium, tantalum, stainless steel, and alloys of the metals, may be selected by one of ordinary skill in the art. In a preferred embodiment, however, the metal is at least one of titanium, aluminum, and vanadium, without any coatings. In a more preferred embodiment, the body 2 and optional integration plate(s) 82 are comprised of titanium or a titanium alloy. An oxide layer may naturally form on a titanium or titanium alloy.

Alternatively, the body 2 may be composed of a non-metal biocompatible material. In one embodiment, the body 2 of the implant 1 is formed of a plastic, polymeric, or composite material. For example, suitable polymers may comprise silicones, polyolefins, polyesters, polyethers, polystyrenes, polyurethanes, acrylates, and co-polymers and mixtures of the polymers. Certain embodiments of the present invention may be comprised of a biocompatible, polymeric matrix reinforced with bioactive fillers, fibers, or both. Certain embodiments of the present invention may be comprised of urethane dimethacrylate (DUDMA)/tri-ethylene glycol dimethacrylate (TEDGMA) blended resin and a plurality of fillers and fibers including bioactive fillers and E-glass fibers. In another embodiment, the body 2 comprises polyetherether-ketone (PEEK), hedrocel, or ultra-high molecular weight polyethylene (UHMWPE). Hedrocel is a composite material composed of carbon and an inert metal, such as tantalum. UHMWPE, also known as high-modulus polyethylene (HMPE) or high-performance polyethylene (HPPE), is a subset of the thermoplastic polyethylene, with a high molecular weight, usually between 2 and 6 million.

Certain embodiments of the interbody spinal implant 1 are substantially hollow and have a generally oval-shaped transverse cross-sectional area. Substantially hollow, as used in this document, means at least about 33% of the interior volume of the interbody spinal implant 1 is vacant. Still further, the substantially hollow portion may be filled with cancellous autograft bone, allograft bone, demineralized bone matrix (DBM), porous synthetic bone graft substitute, bone morphogenic protein (BMP), or combinations of those materials.

Certain embodiments of the present invention may be especially suited for placement between adjacent human vertebral bodies. The implants of the present invention may be used in procedures such as Anterior Lumbar Interbody Fusion (ALIF), Posterior Lumbar Interbody Fusion (PLIF), Transforaminal Lumbar Interbody Fusion (TLIF), and cervical fusion. Certain embodiments do not extend beyond the outer dimensions of the vertebral bodies.

The ability to achieve spinal fusion is directly related to the available vascular contact area over which fusion is desired, the quality and quantity of the fusion mass, and the stability of the interbody spinal implant. Interbody spinal implants, as now taught, allow for improved seating over the apophyseal rim of the vertebral body. Still further, interbody spinal implants, as now taught, better utilize this vital surface area over which fusion may occur and may better bear the considerable biomechanical loads presented through the spinal column with minimal interference with other anatomical or neurological spinal structures. Even further, interbody spinal implants, according to certain aspects of the present invention, allow for improved visualization of implant seating and fusion assessment. Interbody spinal implants, as now taught, may also stimulate osteointegration (e.g., formation of a direct structural and functional interface between the artificial implant and living bone or soft tissue) with the surrounding living bone.

It is generally believed that the surface of an implant determines its ultimate ability to integrate into the surrounding living bone. Without being limited by theory, it is hypothesized that the cumulative effects of at least implant composition, implant surface energy, and implant surface roughness play a major role in the biological response to, and osteointegration of, an implant device. Thus, implant fixation may depend, at least in part, on the stimulation and proliferation of bone modeling and forming cells, such as osteoclasts and osteoblasts and like-functioning cells upon the implant surface. Still further, it appears that these cells attach more readily to relatively rough surfaces rather than smooth surfaces. In this manner, a surface may be bioactive due to its ability to stimulate cellular attachment and osteointegration. The roughened surface topography 80 described in this document may better promote the osteointegration of certain embodiments of the present invention. The roughened surface topography 80 may also better grip the vertebral endplate surfaces and inhibit implant migration upon placement and seating.

Several separate parameters can be used to characterize the roughness of an implant surface. Among those parameters are the average amplitude, Ra; the maximum peak-to-valley height, Rmax; and the mean spacing, Sm. Each of these three parameters, and others, are explained in detail below. Surface roughness may be measured using a laser profilometer or other standard instrumentation.

In addition to the parameters Ra, Rmax, and Sm mentioned above, at least two other parameters can be used to characterize the roughness of an implant surface. In summary, the five parameters are: (1) average amplitude, Ra; (2) average peak-to-valley roughness, Rz; (3) maximum peak-to-valley height, Rmax; (4) total peak-to-valley of waviness profile, Wt; and (5) mean spacing, Sm. Each parameter is explained in detail as follows.

1. Average Amplitude Ra

Figure 19:
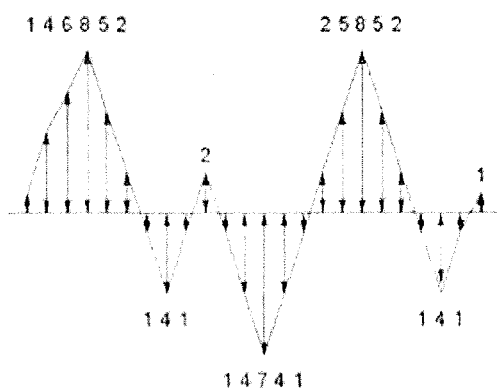
FIG. 19 graphically represents the average amplitude, Ra.

In practice, "Ra" is the most commonly used roughness parameter. It is the arithmetic average height. Mathematically, Ra is computed as the average distance between each roughness profile point and the mean line. In FIG. 19, the average amplitude is the average length of the arrows.

In mathematical terms, this process can be represented as $$Ra = \frac{1}{n}\sum_{i=1}^{n} |y_i|$$

2. Average Peak-to-Valley Roughness Rz

Figure 20:
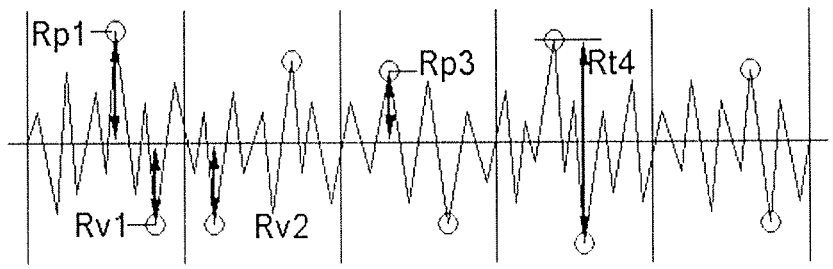
FIG. 20 graphically represents the average peak-to-valley roughness, Rz.

The average peak-to-valley roughness, Rz, is defined by the ISO and ASME 1995 and later. Rz is based on one peak and one valley per sampling length. The RzDIN value is based on the determination of the peak-to-valley distance in each sampling length. These individual peak-to-valley distances are averaged, resulting in the RzDIN value, as illustrated in FIG. 20.

3. Maximum Peak-to-Valley Height Rmax

Figure 21:
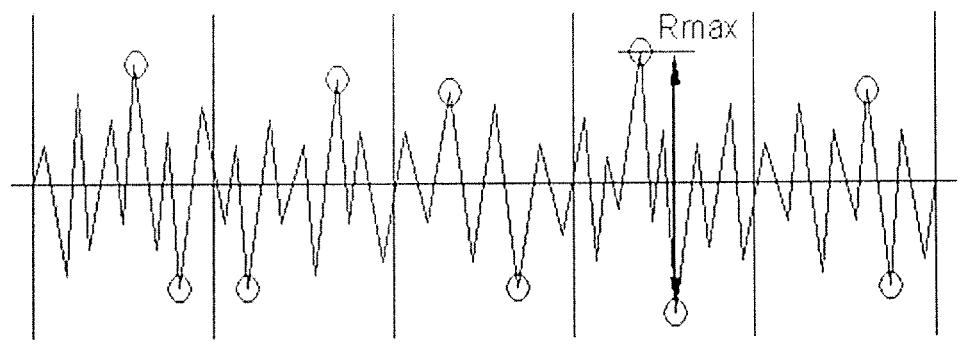
FIG. 21 graphically represents the maximum peak-to-valley height, Rmax.

The maximum peak-to-valley height, Rmax, is the maximum peak-to-valley distance in a single sampling length—as illustrated in FIG. 21.

4. Total Peak-to-Valley of Waviness Profile Wt

Figure 22:
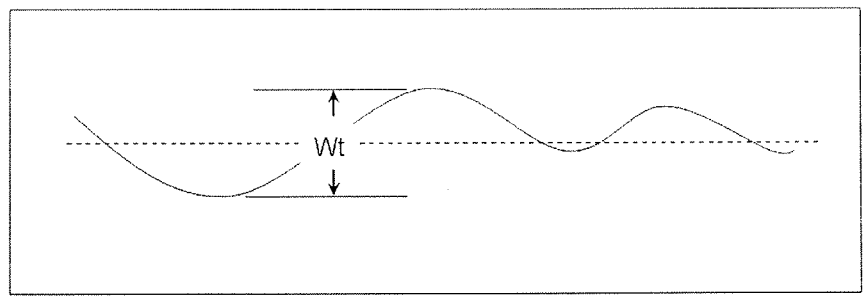
FIG. 22 graphically represents the total peak-to-valley of waviness profile.

The total peak-to-valley of waviness profile (over the entire assessment length) is illustrated in FIG. 22.

5. Mean Spacing Sm

Figure 23:
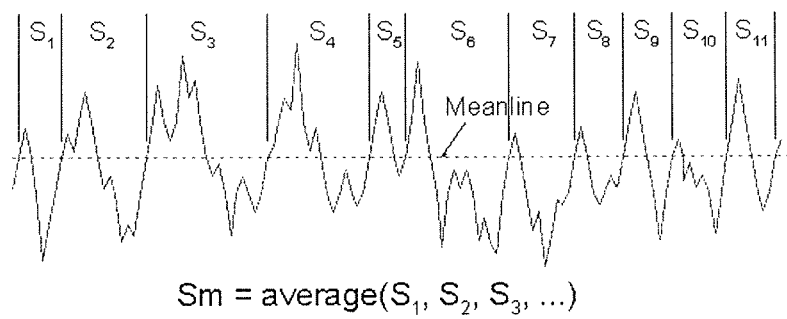
FIG. 23 graphically represents the mean spacing, Sm.

The mean spacing, Sm, is the average spacing between positive mean line crossings. The distance between each positive (upward) mean line crossing is determined and the average value is calculated, as illustrated in FIG. 23.

The parameters Sm, Rmax, and Ra can be used to define the surface roughness following formation of each of the three types of features: macro, micro, and nano.

If present, the following preferred ranges (all measurements in microns) are as follows for the macro features for each of the three parameters. The mean spacing, Sm, is between about 400-2,000, with a range of 750-1,750 preferred and a range of 1,000-1,500 most preferred. The maximum peak-to-valley height, Rmax, is between about 40-500, with a range of 150-400 preferred and a range of 250-300 most preferred. The average amplitude, Ra, is between about 8-200, preferably, 20-200, more preferably 50-150, and most preferably 100-125.

If present, the following preferred ranges (all measurements in microns) are as follows for the micro features for each of the three parameters. The mean spacing, Sm, is between about 20-400, with a range of 100-300 preferred and a range of 200-250 most preferred. The maximum peak-to-valley height, Rmax, is between about 2-40, with a range of 2-20 preferred and a range of 9-13 most preferred. The average amplitude, Ra, is between about 1-20, preferably 2-15, more preferably 4-10, even more preferably 2-8, and most preferably 2-6.

If present, the following preferred ranges (all measurements in microns) are as follows for the nano features for each of the three parameters. The mean spacing, Sm, is between about 0.5-20, with a range of 1-15 preferred and a range of 5-12 most preferred. The maximum peak-to-valley height, Rmax, is between about 0.2-2, with a range of 0.2-1.8 preferred and a range of 0.3-1.3 most preferred. The average amplitude, Ra, is between about 0.01-2, preferably 0.01-1, more preferably, 0.02-0.8, and most preferably 0.03-0.6.

An example of such data is provided in Table 2 below.

Table 2: Example Data by Process Step

Surface Feature Size and Roughness (Metric): Macro (μm)

|  | Size (Sm) | Depth (Rmax) | Roughness (Ra) |
| --- | --- | --- | --- |
| Max. | 2,000 | 500 | 200 |
| Min. | 400 | 40 | 20 |
| Avg. | 1,200 | 270 | 110 |

Surface Feature Size and Roughness (Metric): Micro (μm)

|  | Size (Sm) | Depth (Rmax) | Roughness (Ra) |
| --- | --- | --- | --- |
| Max. | 400 | 40 | 20 |
| Min. | 20 | 2 | 1 |
| Avg. | 210 | 11 | 5.5 |

Surface Feature Size and Roughness (Metric): Nano (μm)

|  | Size (Sm) | Depth (Rmax) | Roughness (Ra) |
| --- | --- | --- | --- |
| Max. | 20 | 2 | 1 |
| Min. | 0.5 | 0.2 | 0.01 |
| Avg. | 10.25 | 1.1 | 0.505 |

Integration Plate(s)

In the case of a composite implant 1, 101, 101*a*, 201, and 301, the integration plate, shown in the drawing as component 82 (FIGS. 12 and 13), 182*a* (FIG. 14), 182 (FIG. 15), 382 (FIG. 16), and 282 (FIG. 17), respectively, includes the roughened surface topography 80, 180, 180*a*, 280, and 380 for the integration surface, and is connectable to either or both of the top surface 10, 110, 110*a*, 210, and 310 or bottom surface 20, 120, 120*a*, 220, and 320. The integration plate 82, 182, 182*a*, 282, and 382 includes a top surface 81, 181, 181*a*, 281, and 381; a bottom surface 83, 183, 183*a*, 283, and 383; an anterior portion 41, 141, 141*a*, 241, and 341; a posterior portion 51, 151, 151*a*, 251, and 351; and at least one vertical aperture 61, 161, 161*a*, 261, and 361. The anterior portion 41, 141, 141*a*, 241, and 341 preferably aligns with the anterior portion 40, 140, 140*a*, 240, and 340 of the main body 2 of the implant 1, 101, 101*a*, 201, and 301, respectively, and the posterior portion 51, 151, 151*a*, 251, and 351 aligns with the posterior portion 50, 150, 150*a*, 250, and 350 of the main body 2 of the implant 1, 101, 101*a*, 201, and 301, respectively. The vertical aperture 61, 161, 161*a*, 261, and 361 preferably aligns with the vertical aperture 60, 160, 160*a*, 260, and 360 of the main body 2 of the implant 1, 101, 101*a*, 201, and 301, respectively. Thus, the integration plate vertical aperture 61, 161, 161*a*, 261, and 361 and the body vertical aperture 60, 160, 160*a*, 260, and 360 preferably comprise substantially the same shape.

The integration plate 82, 182, 182*a*, 282, and 382 may be attached or affixed to the main body of the implant 1, 101, 101*a*, 201, and 301 using any suitable mechanisms known in the art. For example, the bottom surface 83, 183, 183*a*, 283, and 383 of the integration plate 82, 182, 182*a*, 282, and 382 may comprise a reciprocal connector structure, such as a plurality of posts 84, 184, 184*a*, 284, and 384 that align with and insert into a corresponding connector structure such as a plurality of holes 12, 112, 112*a*, 212, and 312 on the top surface 10, 110, 110*a*, 210, and 310 and/or bottom surface 20, 120, 120a, 220, and 320 of the main body 2 of the implant 1, 101, 101a, 201, and 301, respectively, and thus facilitate the connection between the integration plate 82, 182, 182a, 282, and 382 and the main body 2 of the implant 1, 101, 101a, 201, and 301. Thus, integration plates 82, 182, 182a, 282, and 382 with different sizes, shapes, or features may be used in connection with the implant 1, 101, 101a, 201, and 301, for example, to accommodate attributes of the spine of the patient in to which the implant 1, 101, 101a, 201, and 301 is to be implanted. Among these different sizes, shapes, and features are lordotic angles; anti-expulsion edges 8, 108, 108a, 208, and 308; and anti-expulsion angles as described throughout this specification.

The implant 1, 101, 101a, 201, and 301 is configured to receive the integration plate 82, 182, 182a, 282, and 382, respectively. Thus, for example, the top surface 10, 110, 110a, 210, and 310 and/or bottom surface 20, 120, 120a, 220, and 320 of the implant 1, 101, 101a, 201, and 301 may be optionally recessed, and comprise a plurality of holes 12, 112, 112a, 212, and 312 that mate with the plurality of posts 84, 184, 184a, 284, and 384 on the bottom surface 83, 183, 183a, 283, and 383 of the integration plate 82, 182, 182a, 282, and 382. Thus, the plurality of posts 84, 184, 184a, 284, and 384 are inserted into the plurality of holes 12, 112, 112a, 212, and 312.

Figure 14:
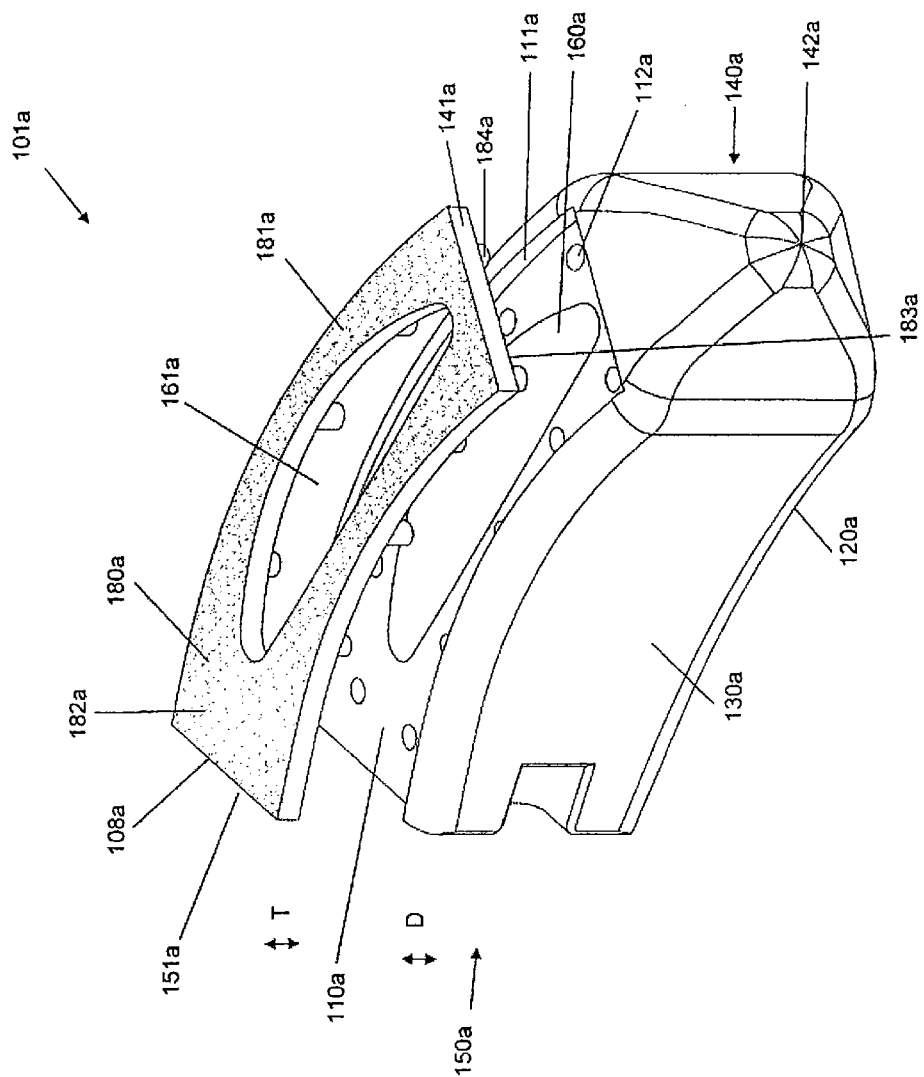
FIG. 14 shows an exploded view of a curved implant with an integration plate.
Figure 15:
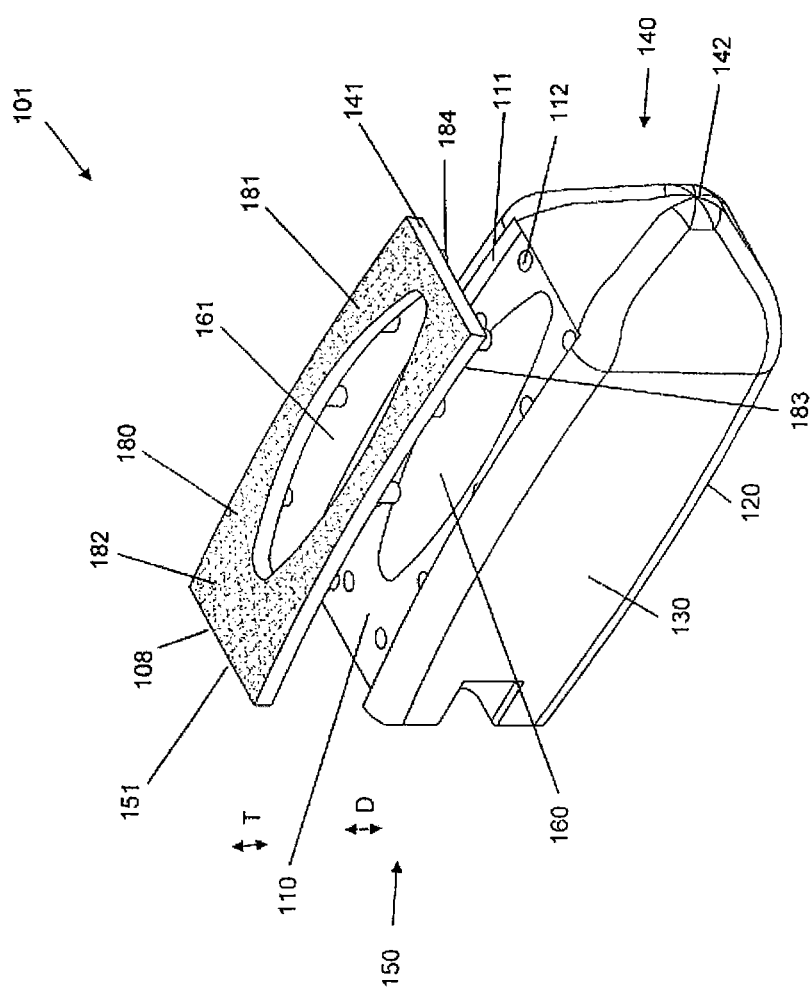
FIG. 15 shows an exploded view of a posterior implant with an integration plate.
Figure 16:
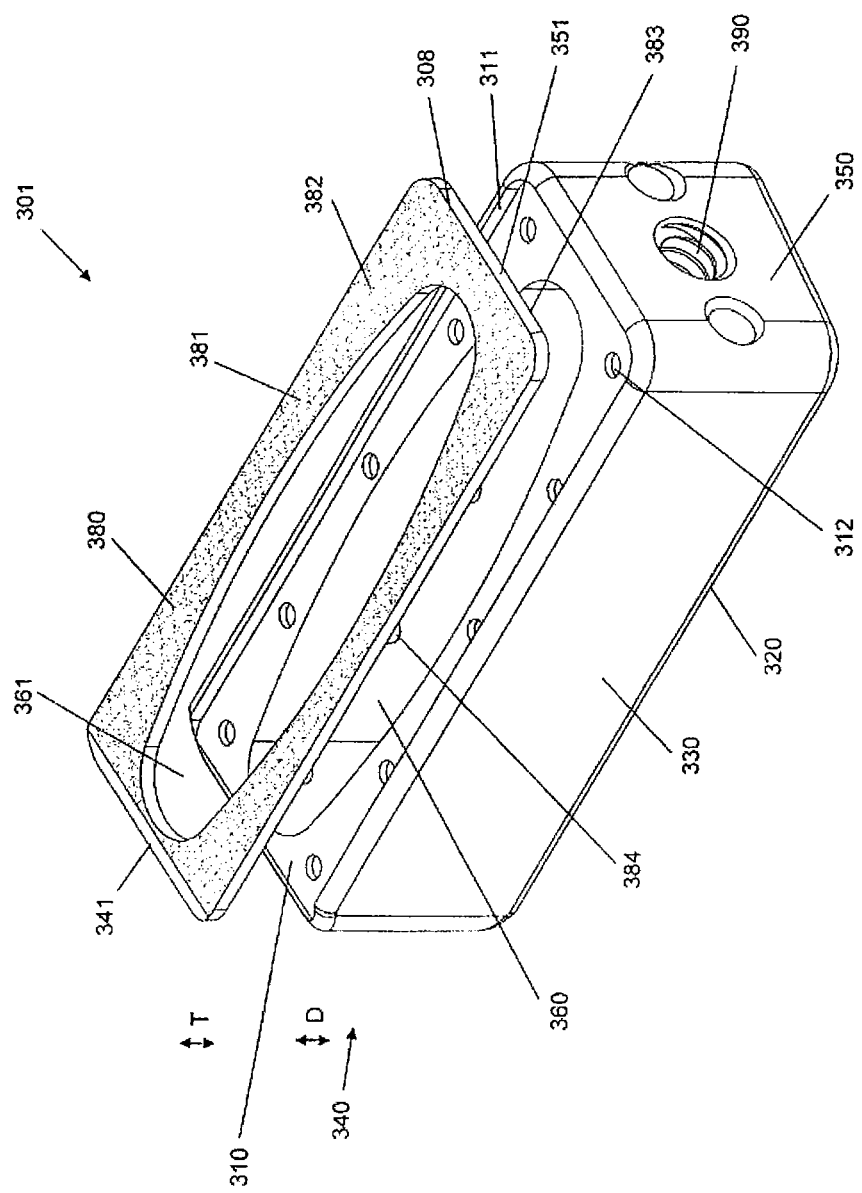
FIG. 16 shows an exploded view of a lateral lumbar implant with an integration plate.
Figure 17:
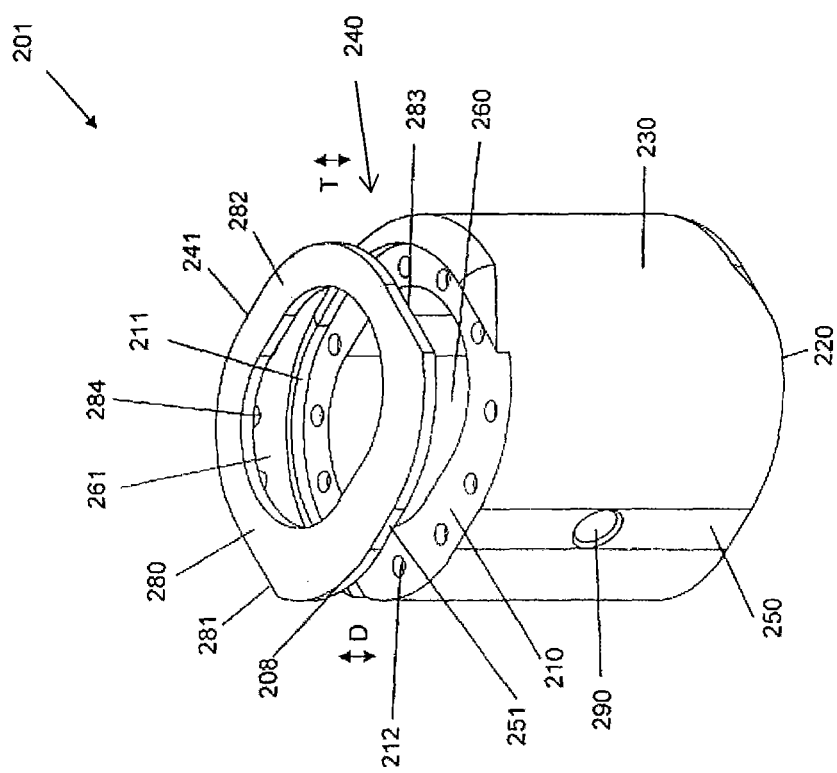
FIG. 17 shows an exploded view of a generally oval-shaped anterior cervical implant with an integration plate.

FIG. 12 shows that the top surface 10 is recessed and comprises a plurality of holes 12, but the recessed bottom surface 20 and its holes 12 are not shown. FIG. 14 shows that the top surface 110a is recessed and comprises a plurality of holes 112a, but the recessed bottom surface 120a and its holes 112a are not shown. FIG. 15 shows that the top surface 110 is recessed and comprises a plurality of holes 112, but the recessed bottom surface 120 and its holes 112 are not shown. FIG. 16 shows that the top surface 310 is recessed and comprises a plurality of holes 312, but the recessed bottom surface 320 and its holes 312 are not shown. FIG. 17 shows that the top surface 210 is recessed and comprises a plurality of holes 212, but the recessed bottom surface 220 and its holes 212 are not shown. The recess may be at a depth D, and the recess depth D preferably is uniform throughout the top surface 10, 110, 110a, 210, and 310 and/or bottom surface 20, 120, 120a, 220, and 320.

The recess depth D preferably corresponds to a thickness T of the integration plate 82, 182, 182a, 282, and 382. Thus, in some aspects, the depth D and thickness T are the same so that once the integration plate 82, 182, 182a, 282, and 382 and body of the implant 1, 101, 101a, 201, and 301, respectively, are placed together, the top surface 10, 110, 110a, 210, and 310 and/or bottom surface 20, 120, 120a, 220, and 320 of the implant 1, 101, 101a, 201, and 301 is substantially even, at least at the seam/junction between the integration plate 82, 182, 182a, 282, and 382 and the top surface 10, 110, 110a, 210, and 310 or bottom surface 20, 210, 120a, 220, and 320. In some embodiments, the posterior portion 51, 151, 151a, 251, and 351 and the anterior portion 41, 141, 141a, 241, and 341 of the integration plate 82, 182, 182a, 282, and 382 have different thicknesses such that the anterior portion 41, 141, 141a, 241, and 341 has a greater thickness than the thickness of the posterior portion 51, 151, 151a, 251, and 351.

The recess depth D and the thickness T may each independently be from about 0.1 mm to about 10 mm. In preferred aspects, the recess depth D and the thickness T may each independently be from about 1 mm to about 5 mm. Thus, for example, the recess depth D or the thickness T may be selected from about 0.1 mm, about 0.25 mm, about 0.5 mm, about 0.75 mm, about 1 mm, about 1.25 mm, about 1.5 mm, about 1.75 mm, about 2 mm, about 2.25 mm, about 2.5 mm, about 2.75 mm, about 3 mm, about 3.25 mm, about 3.5 mm, about 3.75 mm, about 4 mm, about 4.25 mm, about 4.5 mm, about 4.75 mm, about 5 mm, 5.5 mm, about 6 mm, about 6.5 mm, about 7 mm, about 7.5 mm, or about 8 mm.

Recessing the top surface 10, 110, 110a, 210, and 310 or bottom surface 20, 120, 120a, 220, and 320 exposes a ridge 11, 111, 111a, 211, and 311 against which the anterior portion 41, 141, 141a, 241, and 341; posterior portion 51, 151, 151a, 251, and 251; or lateral side of the integration plate 82, 182, 182a, 282, and 382 may be seated when brought together with the implant 1, 101, 101a, 201, and 301.

The integration plate 82, 182, 182a, 282, and 382 may be used with an implant suitable for ALIF (e.g., implant 1, integration plate 82), PLIF (e.g., implant 101, integration plate 182), or TLIF fusion (e.g., implant 101a, integration plate 182a); may be used with an implant suitable for cervical fusion (e.g., implant 201, integration plate 282); and may be used with an implant suitable for lateral lumbar insertion (e.g., implant 301, integration plate 382).

The reciprocal connector such as the post 84, 184, 184a, 284, and 384 preferably is secured within the connector of the body such as the hole 12, 112, 112a, 212, and 312 to mediate the connection between the integration plate 82, 182, 182a, 282, and 382 and the implant 1, 101, 101a, 201, and 301. The connection should be capable of withstanding significant loads and shear forces when implanted in the spine of the patient. The connection between the post 84, 184, 184a, 284, and 384 and the hole 12, 112, 112a, 212, and 312 may comprise a friction fit. In some aspects, the reciprocal connector such as the post 84, 184, 184a, 284, and 384 and the connector of the body such as the hole 12, 112, 112a, 212, and 312 have additional compatible structures and features to further strengthen the connection between the integration plate 82, 182, 182a, 282, and 382 and the implant 1, 101, 101a, 201, and 301.

The structures and features may be on either or both of the integration plate 82, 182, 182a, 282, and 382 and the main body 2 of the implant 1, 101, 101a, 201, and 301. In general, the structures include fasteners, compatibly shaped joints, compatibly shaped undercuts, and/or other suitable connectors having different shapes, sizes, and configurations. For example, a fastener may include a pin, screw, bolt, rod, anchor, snap, clasp, clip, clamp, or rivet. In some aspects, an adhesive may be used to further strengthen any of the integration plate 82, 182, 182a, 282, and 382 and implant 1, 101, 101a, 201, and 301 connections described in this specification. An adhesive may comprise cement, glue, polymer, epoxy, solder, weld, or other suitable binding materials.

The integration plate 82, 182, 182a, 282, and 382 may comprise one or more reciprocal connectors (not shown), such as one or more posts, each having a bore, extending through a horizontal plane. The post may be inserted into a connector such as a hole through the implant 1, 101, 101a, 201, and 301. A fastener (not shown), such as a pin, may be inserted through the bore thereby preventing the post from being disengaged from the hole. In some aspects, the pin may be threaded through a second bore that passes through the walls of the implant 1, 101, 101a, 201, and 301 itself; although it is preferable that the implant 1, 101, 101a, 201, and 301 does not include a second bore through its walls and that the bore is accessible from the space inside of the implant. Alternatively, the integration plate 82, 182, 182a, 282, and 382 may comprise a plurality of bores (not shown) present on and having openings accessible from the bottom of the integration plate 82, 182, 182a, 282, and 382. The bores may mate with a plurality of fasteners, which may comprise rods integral with or otherwise attached to the top surface or bottom surface of the implant 1, 101, 101a, 201, and 301. For example, the rods may be molded as upward-facing extensions or snap-fit into the bores. In some aspects, for example, where the body 2 of the implant 1, 101, 101a, 201, and 301 is comprised of a plastic or polymeric material, the hole 12, 112, 112a, 212, and 312 may not be present, and the screw or bolt (not shown) may be screwed directly into the plastic or polymeric material, with the screw threads tightly gripping the plastic or polymeric material to form the connection.

It is also contemplated that the bottom surface 83, 183, 183a, 283, and 383 of the integration plate 82, 182, 182a, 282, and 382 may comprise undercuts (not shown) in shapes that form a tight junction with compatible shapes on the implant 1, 101, 101a, 201, and 301. For example, the bottom surface 83, 183, 183a, 283, and 383 may comprise a dovetail joint, bevel, or taper that fits with a counterpart dovetail joint, bevel, or taper on the body 2 of the implant 1, 101, 101a, 201, and 301.

An adhesive (not shown) may directly join the integration plate 82, 182, 182a, 282, and 382 and the body 2 of the implant 1, 101, 101a, 201, and 301 together, with or without other connecting features. For example, the adhesive may be applied to the bottom surface 83, 183, 183a, 283, and 383 of the integration plate 82, 182, 182a, 282, and 382. Alternatively, the adhesive may be applied to the top surface 10, 110, 110a, 210, and 310 or bottom surface 20, 120, 120a, 220, and 320 or both surfaces of the implant 1, 101, 101a, 201, and 301.

The foregoing describes various non-limiting examples of how the one or two integration plates 82, 182, 182a, 282, and 382 may be joined together with the implant 1, 101, 101a, 201, and 301.

Other Implant Features

The implant 1 may be machined to comprise some or all of the following implant features, for example. In some aspects, the interbody spinal implant 1 is substantially hollow and has a generally oval-shaped transverse cross-sectional area with smooth, rounded, or both smooth and rounded lateral sides 30 and posterior-lateral corners. The implant 1 includes at least one vertical aperture 60 that extends the entire height of the implant body 2. The vertical aperture 60 defines an interior surface or hollow cavity within the implant 1, which may be filled with bone growth inducing materials. The vertical aperture (a) extends from the top surface to the bottom surface, (b) has a size and shape predetermined to maximize the surface area of the top surface and the bottom surface available proximate the anterior and posterior portions while maximizing both radiographic visualization and access to the substantially hollow center, and (c) optionally defines a transverse rim. The vertical aperture 60 may further define a transverse rim 100 having a greater posterior portion thickness 55 than an anterior portion thickness 45.

In at least one embodiment, the opposing lateral sides 30 and the anterior portion 40 have a rim thickness 45 of about 5 mm, while the posterior portion 50 has a rim thickness 55 of about 7 mm. Thus, the rim posterior portion thickness 55 may allow for better stress sharing between the implant 1 and the adjacent vertebral endplates and helps to compensate for the weaker posterior endplate bone. In some aspects, the transverse rim 100 has a generally large surface area and contacts the vertebral endplate. The transverse rim 100 may act to better distribute contact stresses upon the implant 1, and hence minimize the risk of subsidence while maximizing contact with the apophyseal supportive bone. It is also possible for the transverse rim 100 to have a substantially constant thickness (e.g., for the anterior portion thickness 45 to be substantially the same as the posterior portion thickness 55) or for the posterior portion 50 to have a rim thickness 55 less than that of the opposing lateral sides 30 and the anterior portion 40.

The implant 1 may be shaped to reduce the risk of subsidence, and improve stability, by maximizing contact with the apophyseal rim of vertebral endplates. Embodiments may be provided in a variety of anatomical footprints having a medial-lateral width ranging from about 32 mm to about 44 mm. An interbody spinal implant 1 generally does not require extensive supplemental or obstructive implant instrumentation to maintain the prepared disc space during implantation. Thus, the interbody spinal implant 1 and associated implantation methods allow for larger-sized implants as compared with other size-limited interbody spinal implants known in the art. This advantage allows for greater medial-lateral width and correspondingly greater contact with the apophyseal rim.

Figure 13:
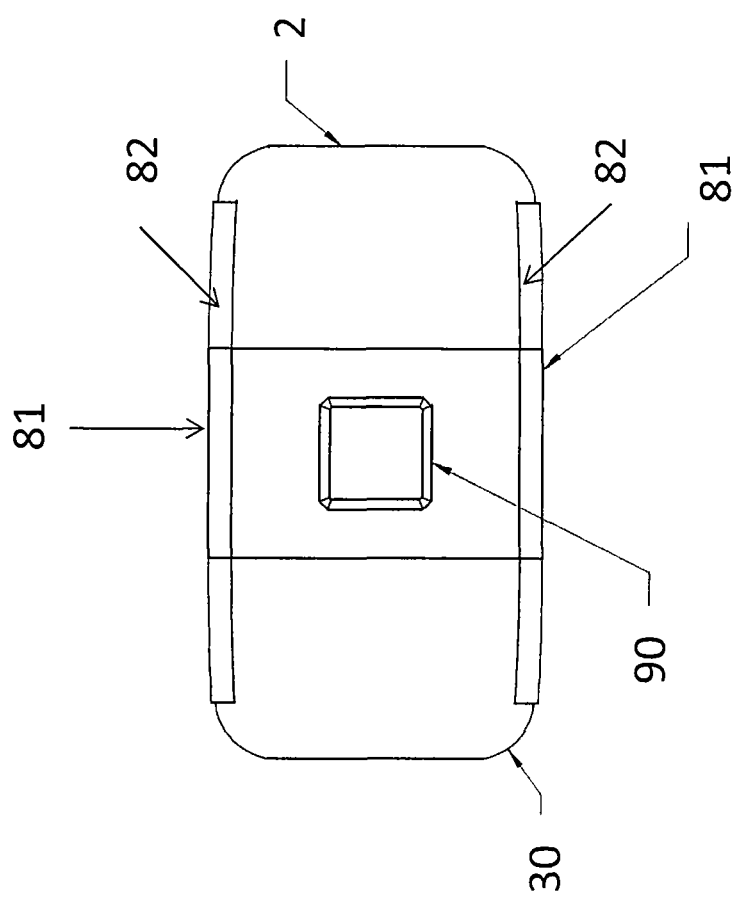
FIG. 13 shows an anterior view of an embodiment of the interbody spinal implant having two integration plates, which sandwich the body of the implant.

As illustrated in FIGS. 12 and 13, the implant 1 has an opening 90 in the anterior portion 40. In one embodiment, the posterior portion 50 may have a similarly shaped opening 90 (not shown). In some aspects, only the anterior portion 40 has the opening 90 while the posterior portion 50 has an alternative opening 92 (which may have a size and shape different from the opening 90). The opening 92 defines an interior surface or hollow cavity, which may be filled with bone growth inducing materials.

The opening 90, 290, and 390 has a number of functions. One function is to facilitate manipulation of the implant 1, 201, and 301 by the caretaker. Thus, the caretaker may insert a surgical tool into the opening 90, 290, and 390 and, through the engagement between the surgical tool and the opening 90, 290, and 390, manipulate the implant 1, 201, and 301. The opening 90, 290, and 390 may be threaded to enhance the engagement. A suitable surgical tool, such as a distractor (not shown), may be selected by one of ordinary skill in the art.

As best shown in FIGS. 14 and 15, the anterior portion 140, 140a may have a tapered nose 142, 142a to facilitate insertion of the implant 101.

The implant 1 may further include at least one transverse aperture 70 that extends the entire transverse length of the implant body. The transverse aperture 70 defines an interior surface or hollow cavity, which may be filled with bone growth inducing materials. The at least one transverse aperture 70 may provide improved visibility of the implant 1 during surgical procedures to ensure proper implant placement and seating, and may also improve post-operative assessment of implant fusion. The transverse aperture 70 may be broken into two, separate sections by an intermediate wall. Suitable shapes and dimensions for the transverse aperture 70 may be selected by one of ordinary skill in the art. In particular, all edges of the transverse aperture 70 may be rounded, smooth, or both. The intermediate wall may be made of the same material as the remainder of the body 2 of the implant 1 (e.g., plastic), or it may be made of another material (e.g., metal). The intermediate wall may offer one or more of several advantages, including reinforcement of the implant 1 and improved bone graft containment.

The implant 1 may be provided with a solid rear wall (not shown). The rear wall may extend the entire width of the implant body and nearly the entire height of the implant body. Thus, the rear wall can essentially close the anterior portion 40 of the implant 1. The rear wall may offer one or more of several advantages, including reinforcement of the implant 1 and improved bone graft containment. In the cervical application, it may be important to prevent bone graft material from entering the spinal canal.

The implant 1 may also have a lordotic angle to facilitate alignment. The anterior portion 40 is preferably generally greater in height than the opposing posterior portion 50. Therefore, the implant 1 may better compensate for the generally less supportive bone found in certain regions of the vertebral endplate. As much as seven degrees of lordosis (or more) may be built into the implant 1 to help restore cervical balance.

To enhance movement resistance and provide additional stability under spinal loads in the body, the implant 1, 101, 101a, 201, and 301 may comprise one or more anti-expulsion edges 8, 108, 108a, 208, and 308 that tend to "dig" into the end-plates slightly and help to resist expulsion. The anti-expulsion edges 8, 108, 108a, 208, and 308 may be present on the top surface 81 of the integration plate 82 affixed to the top surface 10, 110, 110a, 210, and 310; the bottom surface 20, 120, 120a, 220, and 320; or both surfaces of the implant 1, 101, 101a, 201, and 301. Alternatively, the anti-expulsion edges 8, 108, 108a, 208, and 308 may be present on the top surface 10, 110, 110a, 210, and 310; the bottom surface 20, 120, 120a, 220, and 320; or both surfaces of the body of the implant 1, 101, 101a, 201, and 301.

By way of example, FIG. 12 shows an anti-expulsion edge 8 on the top surface 81 of the integration plate 82 and the bottom surface 20 of the anterior face 40 of the implant 1. Each anti-expulsion edge 8 may protrude above the plane of the top surface 81 of the integration plate 82 and bottom surface 20, with the amount of protrusion increasing toward the anterior face 40 and the highest protrusion height P at the anterior-most edge of the top surface 81 of the integration plate 82 or bottom surface 20.

An anti-expulsion edge 8, 108, 108a, 208, and 308 may be oriented toward the anterior portion 40, 140, 140a, 240, and 340, or the posterior portion 50, 150, 150a, 250, and 350, or either of the opposing lateral sides 30, 130, 130a, 230, and 330. The orientation of the anti-expulsion edge 8, 108, 108a, 208, and 308 may depend on the intended orientation of the implant 1, 101, 101a, 201, and 301 when it has been implanted between vertebrae in the patient.

Example Surgical Methods

The following examples of surgical methods are included to more clearly demonstrate the overall nature of the invention. These examples are exemplary, not restrictive, of the invention.

Certain embodiments of the invention are particularly suited for use during interbody spinal implant procedures currently known in the art. For example, the disc space may be accessed using a standard mini open retroperitoneal laparotomy approach. The center of the disc space is located by AP fluoroscopy taking care to make sure the pedicles are equidistant from the spinous process. The disc space is then incised by making a window in the annulus for insertion of certain embodiments of the spinal implant 1, 101, 101a, 201, and 301 (a 32 or 36 mm window in the annulus is typically suitable for insertion). The process according to the invention minimizes, if it does not eliminate, the cutting of bone. The endplates are cleaned of all cartilage with a curette, however, and a size-specific rasp (or broach) may then be used.

Use of a rasp preferably substantially minimizes or eliminates removal of bone, thus substantially minimizing or eliminating impact to the natural anatomical arch, or concavity, of the vertebral endplate while preserving much of the apophyseal rim. Preservation of the anatomical concavity is particularly advantageous in maintaining biomechanical integrity of the spine. For example, in a healthy spine, the transfer of compressive loads from the vertebrae to the spinal disc is achieved via hoop stresses acting upon the natural arch of the endplate. The distribution of forces, and resultant hoop stress, along the natural arch allows the relatively thin shell of subchondral bone to transfer large amounts of load.

During traditional fusion procedures, the vertebral endplate natural arch may be significantly removed due to excessive surface preparation for implant placement and seating. This is especially common where the implant 1, 101, 101a, 201, and 301 is to be seated near the center of the vertebral endplate or the implant 1, 101, 101a, 201, and 301 is of relatively small medial-lateral width. Breaching the vertebral endplate natural arch disrupts the biomechanical integrity of the vertebral endplate such that shear stress, rather than hoop stress, acts upon the endplate surface. This redistribution of stresses may result in subsidence of the implant 1, 101, 101a, 201, and 301 into the vertebral body.

Preferred embodiments of the surgical method minimize endplate bone removal on the whole, while still allowing for some removal along the vertebral endplate far lateral edges where the subchondral bone is thickest. Still further, certain embodiments of the interbody spinal implant 1, 101, 101a, 201, and 301 include smooth, rounded, and highly radiused posterior portions and lateral sides which may minimize extraneous bone removal for endplate preparation and reduce localized stress concentrations. Thus, interbody surgical implant 1, 101, 101a, 201, and 301 and methods of using it are particularly useful in preserving the natural arch of the vertebral endplate and minimizing the chance of implant subsidence.

Because the endplates are spared during the process of inserting the spinal implant 1, 101, 101a, 201, and 301, hoop stress of the inferior and superior endplates is maintained. Spared endplates allow the transfer of axial stress to the apophasis. Endplate flexion allows the bone graft placed in the interior of the spinal implant 1, 101, 101a, 201, and 301 to accept and share stress transmitted from the endplates. In addition, spared endplates minimize the concern that BMP might erode the cancellous bone.

Interbody spinal implant 1, 101, 101a, 201, and 301 is durable and can be impacted between the endplates with standard instrumentation. Therefore, certain embodiments of the invention may be used as the final distractor during implantation. In this manner, the disc space may be under-distracted (e.g., distracted to some height less than the height of the interbody spinal implant 1) to facilitate press-fit implantation. Further, certain embodiments of the current invention having a smooth and rounded posterior portion (and lateral sides) may facilitate easier insertion into the disc space. Still further, the surface roughened topography 80 may lessen the risk of excessive bone removal during distraction as compared to implants having teeth, ridges, or threads currently known in the art even in view of a press-fit surgical distraction method. Nonetheless, once implanted, the interbody surgical implant 1, 101, 101a, 201, and 301 may provide secure seating and prove difficult to remove. Thus, certain embodiments of the interbody spinal implant 1, 101, 101a, 201, and 301 may maintain a position between the vertebral endplates due, at least in part, to resultant annular tension attributable to press-fit surgical implantation and, post-operatively, improved osteointegration.

Surgical implants and methods according to embodiments of the invention tension the vertebral annulus via distraction. These embodiments may also restore spinal lordosis, thus improving sagittal and coronal alignment. Implant systems currently known in the art require additional instrumentation, such as distraction plugs, to tension the annulus. These distraction plugs require further tertiary instrumentation, however, to maintain the lordotic correction during actual spinal implant insertion. If tertiary instrumentation is not used, then some amount of lordotic correction may be lost upon distraction plug removal. Interbody spinal implant 1, 101, 101a, 201, and 301, according to certain embodiments of the invention, is particularly advantageous in improving spinal lordosis without the need for tertiary instrumentation, thus reducing the instrument load upon the surgeon. This reduced instrument load may further decrease the complexity, and required steps, of the implantation procedure.

Certain embodiments of the spinal implant 1, 101, 101a, 201, and 301 may also reduce deformities (such as isthmic spondylolythesis) caused by distraction implant methods. Traditional implant systems require secondary or additional instrumentation to maintain the relative position of the vertebrae or distract collapsed disc spaces. In contrast, interbody spinal implant 1, 101, 101a, 201, and 301 may be used as the final distractor and thus maintain the relative position of the vertebrae without the need for secondary instrumentation.

Certain embodiments collectively comprise a family of implants, each having a common design philosophy. These implants 1, 101, 101a, 201, and 301 and the associated surgical technique have been designed to address at least the ten, separate challenges associated with the current generation of traditional anterior spinal fusion devices listed above in the Background section of this document.

After desired annulotomy and discectomy, embodiments of the invention first adequately distract the disc space by inserting (through impaction) and removing sequentially larger sizes of very smooth distractors, which have been size matched with the size of the available implant 1, 101, 101a, 201, and 301. Once adequate distraction is achieved, the surgeon prepares the end-plate with a rasp. There is no secondary instrumentation required to keep the disc space distracted while the implant 1, 101, 101a, 201, and 301 is inserted, as the implant 1, 101, 101a, 201, and 301 has sufficient mechanical strength that it is impacted into the disc space. In fact, the height of the implant 1, 101, 101a, 201, and 301 is preferably about 1 mm greater than the height of the rasp used for end-plate preparation, to create some additional tension in the annulus by implantation, which creates a stable implant construct in the disc space.

The implant geometry has features which allow it to be implanted via any one of an anterior, antero-lateral, or lateral approach, providing tremendous intra-operative flexibility of options. The implant 1, 101, 101a, 201, and 301 has adequate strength to allow impact, and the sides of the implant 1, 101, 101a, 201, and 301 may have smooth surfaces to allow for easy implantation and, specifically, to prevent binding of the implant 1, 101, 101a, 201, and 301 to soft tissues during implantation.

The invention encompasses a number of different implant 1, 101, 101a, 201, and 301 configurations, including a composite implant 1, 101, 101a, 201, and 301 formed of top and optional bottom plates (components), for example, made out of titanium. The integration surfaces exposed to the vertebral body have a roughened surface topography 80 to allow for bony in-growth over time, and to provide resistance against expulsion. The top and bottom titanium plates may be assembled together with the implant body 2. The net result is a composite implant 1, 101, 101a, 201, and 301 that has engineered stiffness for its clinical application. The axial load may be borne by the polymeric component of the construct.

It is believed that an intact vertebral end-plate deflects like a diaphragm under axial compressive loads generated due to physiologic activities. If a spinal fusion implant 1, 101, 101a, 201, and 301 is inserted in the prepared disc space via a procedure which does not destroy the end-plates, and if the implant 1, 101, 101a, 201, and 301 contacts the end-plates only peripherally, the central dome of the end-plates can still deflect under physiologic loads. This deflection of the dome can pressurize the bone graft material packed inside the spinal implant, hence allowing it to heal naturally. The implant 1, 101, 101a, 201, and 301 designed according to certain embodiments allows the vertebral end-plate to deflect and allows healing of the bone graft into fusion.

Although illustrated and described above with reference to certain specific embodiments and examples, the present invention is nevertheless not intended to be limited to the details shown. Rather, various modifications may be made in the details within the scope and range of equivalents of the claims and without departing from the spirit of the invention. It is expressly intended, for example, that all ranges broadly recited in this document include within their scope all narrower ranges which fall within the broader ranges. In addition, features of one embodiment may be incorporated into another embodiment.

What is claimed is:

1. A process of producing an interbody spinal implant having a regular repeating pattern, the process comprising:
    applying a protective maskant to an entire interbody spinal implant, the interbody spinal implant including a body that is generally oval-shaped in transverse cross section, and comprises a top surface, a bottom surface, opposing lateral sides, opposing anterior and posterior portions, a substantially hollow center, anti-expulsion edges at the junction of the anterior portion and the top surface and at the junction of the anterior portion and the bottom surface to resist pullout of the implant once inserted in an intervertebral space, generally rounded and blunt intersections defined along the entire lengths between the top surface and the lateral sides and the bottom surface and the lateral sides, and a single vertical aperture extending from the top surface to the bottom surface, having a maximum width at its center, and defining a transverse rim on the top surface and on the bottom surface, said transverse rim having a posterior thickness greater than an anterior thickness;
    removing a portion of the protective maskant to expose a base surface of at least one of the top surface of the body and the bottom surface of the body; and
    applying at least one additive process or subtractive process to at least a portion of the exposed base surface to form a regular repeating pattern, wherein at least one of the top surface and the bottom surface of the interbody spinal implant has the regular repeating pattern and the smooth rounded edge along the top of each lateral side and the top of the anterior portion does not have the regular repeating pattern.

2. The process of claim 1 further comprising applying a second maskant to the exposed base surface-in a pattern before applying the at least one additive process or subtractive process to provide a masked portion of the exposed base surface-protected by the second maskant and an unmasked portion of the exposed base surface not protected by the second maskant.

3. The process of claim 2, wherein the second maskant is applied via sputtering, deposition, or evaporation.

4. The process of claim 2, wherein the second maskant is applied in an array of strips, dots, circles, ovals, squares, triangles, or amorphous shapes.

5. The process of claim 4, wherein the second maskant is applied automatically by an ink jet printing system.

6. The process of claim 2, wherein the exposed base surface is subjected to the subtractive process to remove the unmasked portion of the exposed base surface not protected by the second maskant.

7. The process of claim 6, wherein the subtractive process comprises acid etching.

8. The process of claim 1, wherein the additive process is applied to the base surface and the additive process produces an array of strips, dots, spheres, semi-spheres, cubes, polyhedral pyramids, or amorphous shapes on the base surface.

9. The process of claim 8, wherein the additive process is applied via sputtering, deposition, evaporation, welding, impacting, or injecting.

10. The process of claim 1, wherein the at least one additive process or subtractive process is applied repeatedly to form an overlapping surface pattern.

11. The process of claim 1, wherein the at least one additive process or subtractive process comprises macro processing, micro processing, and optionally, nano processing.

12. The process of claim 11, wherein the macro processing includes heavy mechanical or chemical bulk removal; the micro processing includes mechanical or chemical removal; and the nano processing includes mild chemical etching, laser or other directed energy material removal, abrasion, blasting, or tumbling.

13. The process of claim 1, wherein the regular repeating pattern is oriented in opposition to biologic forces on the implant and to an insertion direction and promotes bone growth, fusion, and healing responses.

14. The process of claim 1, wherein the regular repeating pattern comprises a roughness average amplitude, Ra, of about 1-200.

15. The process of claim 1, wherein the body, comprises titanium or a titanium alloy.

16. The process of claim 1, wherein the single vertical aperture of the body (a) extends from the top surface to the bottom surface of the body, (b) has a size and shape predetermined to maximize the surface area of the top surface and the bottom surface available proximate the anterior and posterior portions while maximizing both radiographic visualization and access to the substantially hollow center, and (c) defines a transverse rim having a varying thickness.

17. The process of claim 1, wherein
applying at least one additive process or subtractive process to the exposed base surface to form a regular repeating pattern comprises repeatedly applying an additive process to form a roughened surface topography without sharp teeth.

18. The process of claim 1, wherein
applying at least one additive process or subtractive process to the exposed base surface to form a regular repeating pattern comprises repeatedly applying a subtractive process to form a roughened surface topography without sharp teeth.

19. The process of claim 1, wherein the subtractive process is used and prior to applying the subtractive process, (a) applying a first maskant in a first pattern and applying a second maskant in a second pattern; and (b) subsequently applying a chemical etchant.

20. The process of claim 1, wherein the additive process is used and includes applying a first pattern of protrusions, applying a second pattern of protrusions, and applying a third pattern of protrusions.

* * * * *